United States Patent [19]
Sakai et al.

[11] 3,971,825
[45] July 27, 1976

[54] PHARMACEUTICALLY USEFUL PROSTENOIC ACID DERIVATIVES

[75] Inventors: Kiyoshi Sakai; Takashi Yusa; Kenji Inoue, all of Tokyo, Japan

[73] Assignee: Sankyo Company Limited, Tokyo, Japan

[22] Filed: Nov. 26, 1974

[21] Appl. No.: 527,353

[30] Foreign Application Priority Data
Dec. 6, 1973 Japan.............................. 48-137588

[52] U.S. Cl................ 260/514 D; 260/247.2 R; 260/268 R; 260/293.65; 260/326.2; 260/410.9 R; 260/413; 260/468 D; 260/488 R; 260/501.1; 260/501.15; 260/501.17; 260/501.2; 260/240 R; 424/305; 424/317
[51] Int. Cl.²................... C07C 61/38; C07C 69/74
[58] Field of Search..................... 260/468 D, 514D

[56] References Cited
UNITED STATES PATENTS
3,886,206    5/1975    Crabbe et al........................ 260/514

*Primary Examiner*—Robert Gerstl
*Attorney, Agent, or Firm*—Flynn & Frishauf

[57] ABSTRACT

New prostaglandin-like compounds, having brochodilating activity, of formula

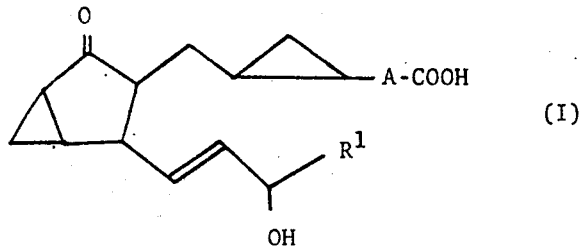

(I)

(wherein A represents a direct bond or an alkylene group and $R^1$ represents an alkyl group) and their pharmaceutically acceptable salts are prepared by oxidizing compounds of formula

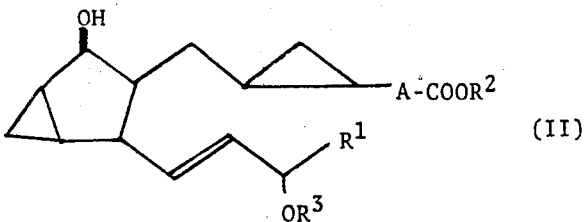

(II)

(wherein $R^2$ represents hydrogen or a carboxyl-protecting group, and $R^3$ represents a hydroxyl-protecting group), removing protecting groups from the product and, when appropriate, salifying the compound obtained.

12 Claims, No Drawings

PHARMACEUTICALLY USEFUL PROSTENOIC ACID DERIVATIVES

This invention relates to pharmaceutically useful prostenoic acid derivatives.

The invention provides prostenoic acid derivatives having the formula

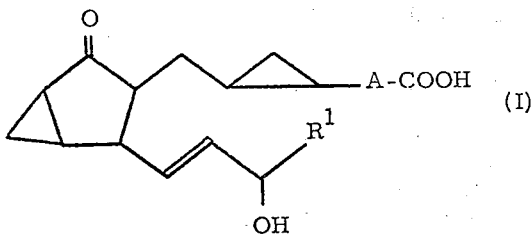

wherein:

A represents a direct bond or an alkylene group; and
$R^1$ represents an alkyl group;
and pharmaceutically acceptable salts thereof.

In formula (I), when A represents a direct bond the carboxyl group is directly connected to the three-membered ring of the side chain. When A represents an alkylene group, it can be straight or branched and may be, for example, methylene, ethylene, trimethylene, 1-methylethylene, 2-methylethylene, tetramethylene, 1-methyltrimethylene, 2-methyltrimethylene, 3-methyltrimethylene, 1,2-dimethylethylene, 2-ethylethylene, pentamethylene, 1-methyltetramethylene, 2-methyltetramethylene, 4-methyltetramethylene, 1,1-dimethyltrimethylene, 1,2-dimethyltrimethylene, 1,3-dimethyltrimethylene, 3-ethyltrimethylene, 1-methyl-2-ethylethylene, hexamethylene, 1-methylpentamethylene, 2-methylpentamethylene, 3-methylpentamethylene, 1,1-dimethyltetramethylene, 1,2-dimethyltetramethyylene, 1,3-dimethyltetramethylene, 1,4-dimethyltetramethylene, 2,2-dimethyltetramethylene, 3,3-dimethyltetramethylene, 2,3-dimethyltetramethylene, 2,4-dimethyltetramethylene, 1-ethyltetramethylene, 2,-ethyltetramethylene, 1-methyl-3-ethyltrimethylene, heptamethylene, 1-methylhexamethylene, 2-methylhexamethylene, 3-methylhexamethylene, 4-methylhexamethylene, 5-methylhexamethylene, 6-methylhexamethylene, 1,1-dimethylpentamethylene, 1,2-dimethylpentamethylene, 1,3-dimethylpentamethylene, 1,4-dimethylpentamethylene, 1,5-dimethylpentamethylene, 2,2-dimethylpentamethylene, 3,3-dimethylpentamethylene, 4,4-dimethylpentamethylene, 5,5-dimethylpentamethylene, 1-methyl-3-ethyltetramethylene, octamethylene, 3-methylheptamethylene or 3,3-dimethylhexamethylene. Straight or branched alkylene groups having from 1 to 8 carbon atoms are preferred, especially those having from 1 to 5 carbon atoms.

The group $R^1$ in formula (I) can be a straight or branched alkyll group, for example methyl, ethyl, n-propyl, isopropyl, n-butyl, isobutyl, s-butyl, t-butyl, n-pentyl, isopentyl, s-amyl, t-amyl, n-hexyl, 2-hexyl, 2-methylpentyl, 3-methylpentyl, 4-methylpentyl, 3-hexyl, 2-ethylbutyl, 2-methyl-2-pentyl, 2,2-dimethylbutyl, n-heptyl, 2-heptyl, 3-heptyl, 2-methylhexyl, 3-methylhexyl, 4-methylhexyl, 5-methylhexyl, 2-methyl-2-hexyl, 3-methyl-2-hexyl, 4-methyl-2-hexyl, 2,2-dimethylpentyl, 2,3-dimethylpentyl, n-octyl, 2-octyl, 3-octyl, 3-methyl-3-heptyl, 2-ethyl-2-methylpentyl, 4-methyl-3-heptyl, 3-ethyl-2-hexyl, n-nonyl, 2-nonyl, 3-nonyl, 3-methyl-3-octyl, 3-ethyl-3-heptyl, 4-methyl-3-octyl, 2,2-diethylhexyl or n-decyl. In general, straight or branched alkyl groups having from 1 to 10 carbon atoms are preferred, especially those having from 4 to 10 carbon atoms.

The compounds of formula (I) and their pharmaceutically acceptable salts can exist in the form of various geometrical and optical isomers. All the individual isomers and their mixtures are included within the scope of the invention.

The compounds of formula (I) can be salified by the conventional techniques, to form pharmaceutically acceptable salts. These include alkali and alkaline earth metal salts (e.g. the sodium, potassium, magnesium and calcium salts), the ammonium salts, quaternary ammonium salts (e.g. the tetramethylammonium, tetraethylammonium, benzyltrimethylammonium and phenyltriethylammonium salts), aliphatic, alicyclic or aromatic amine salts (e.g. the methylamine, ethylammine, dimethylamine, diethylamine, trimethylamine, triethylamine, N-methylhexylamine, cyclopentylamine, dicyclohexylamine, benzylamine, dibenzylamine, α-phenylethylamine and ethylenediamine salts), heterocyclic amine salts (e.g. the piperidine, morpholine, pyrrolidine, piperazine, pyridine, 1-methylpiperazine and 4-ethylmorpholine salts), and salts of amines which contain a hydrophilic group (e.g. the monoethanolamine, ethyldiethanolamine and 2-amino-1-butanol salts).

The following compounds of formula (1) and their pharmaceutically acceptable salts are specific examples of the compounds provided by the invention:

1. 9-Oxo-15α(or β)-hydroxy-5(6), 10(11)α-bis-methyleneprost-13-transenoic acid;
2. 9-Oxo-15α(or β)-hydroxy-5(6),10(11)α-bis-methyleneisoprost-13-trans-enoic acid;
3. 9-Oxo-15α(or β)-hydroxy-16-methyl-5(6),10(11)α-bis-methyleneprost-13-trans-enoic acid;
4. 9-Oxo-15α(or β)-hydroxy-16-methyl-5(6),10(11)α-bis-methyleneisoprost-13-trans-enoic acid;
5. 9-Oxo-15α(or β)-hydroxy-16,16-dimethyl-5(6), 10(11)α-bis-methyleneprost-13-trans-enoic acid;
6. 9-Oxo-15α(or β)-hydroxy-16, 16-dimethyl-5(6),10(11)α-bis-methyleneisoprost-13-trans-enoic acid;
7. 9-Oxo-15α(or β)-hydroxy-20-methyl-5(6),10(11)α-bis-methyleneprost-13-trans-enoic acid;
8. 9-Oxo-15α(or β)-hydroxy-20-methyl-5(6), 10(11)α-bis-methyleneisoprost-13-trans-enoic acid;
9. 9-Oxo-15α(or β)-hydroxy-20-ethyl-5(6), 10(11)α-bis-methyleneprost-13-trans-enoic acid;
10. 9-Oxo-15α(or β)-hydroxy-20-ethyl-5(6), 10(11)α-bis-methyleneisoprost-13-trans-enoic acid;
11. 9-Oxo-15α(or β)-hydroxy-20-n-propyl-5(6),10(11)α-bis-methyleneprost-13-trans-enoic acid;
12. 9-Oxo-15α(or β)-hydroxy-20-n-propyl-5(6),10(11)α-bis-methyleneisoprost-13-trans-enoic acid;
13. 9-Oxo-15α(or β)-hydroxy-20-n-butyl-5(6), 10(11)α-bis-methyleneprost-13-trans-enoic acid;
14. 9-Oxo-15α(or β)-hydroxy-20-n-butyl-5(6),10(11)α-bis-methyleneisoprost-13-trans-enoic acid;
15. 9-Oxo-15α(or β)-hydroxy-5(6),10(11)α-bis-methylene-ω-norprost-13-trans-enoic acid;

16. 9-Oxo-15α(or β)-hydroxy-5(6),10(11)α-bis-methylene-ω-norisoprost113-trans-enoic acid;
17. 10-Oxo-16α(or β)-hydroxy-6(7),11(12)α-bis-methylenehomoprost-14-trans-enoic acid;
18. 10-Oxo-16α(or β)-hydroxy-6(7),11(12)α-bis-methylenehomoisoprost-14-trans-enoic acid;
19. 8-Oxo-14α(or β)-hydroxy-4(5),9(10)α-bis-methylenenorprost-12-trans-enoic acid;
20. 8-Oxo-14α(or β)-hydroxy-4(5), 9(10)α-bis-methylenenorisoprost-12-trans-enoic acid;
21. 7-Oxo-13α(or β)-hydroxy-3(4),8(9)α-bis-methylenedinorprost-11-trans-enoic acid;
22. 7-Oxo-13α(or β)-hydroxy-3(4),8(9)α-bis-methylenedinorisoprost-11-trans-enoic acid;
23. 6-Oxo-12α(or β)-hydroxy-2(3),7(8)α-bis-methylenetrinorprost-10-trans-enoic acid; and
24. 6-Oxo-12α(or β)-hydroxy-2(3),7(8)α-bis-methylenetrinorisoprost-10-trans-enoic acid.

The compounds of the invention exhibit pharmacological activity. Specifically, in animal tests they have been shown to act as bronchodilators. As an example of such a test, guinea-pigs with a body weight of 400–600 g, anaesthetised with pentobarbital sodium, were given 2.5–5 μg/kg of 9-oxo-15α-hydroxy-5(6),10(11)α-bis-methyleneprost-13-trans-enoic acid, as a compound of formula (I), and 2–3 μg/kg of histamine were injected intravenously. The effect on resistance in the air-passages was determined by a variant of the Konzett-Rössler method — Archiv für Expermentelle Pathologie und Pharmakologie, Vol. 195, 71(1940) — and it was found that the compound of formula (I) had an activity of the same order as that of prostaglandin $E_2$. On the other hand, the compounds of the invention exhibit only very weakly other types of prostaglandin activity, such as oxytocic activity.

Accordingly, the compounds of the invention are useful as pharmaceuticals when a specific bronchodilating activity is required, and can be formulated into pharmaceutical compositions together with a pharmaceutical excipient, in the conventional manner. They are generally formulated for inhalation as an aerosol spray, in a pressurized container, with a pharmaceutically acceptable propellant. Optimum dosage varies with the body weight, age and condition of the patient, but is generally from 50 to 150 μg per day for adults.

The compounds of formula (I) can be obtained by oxidizing a compound of formula

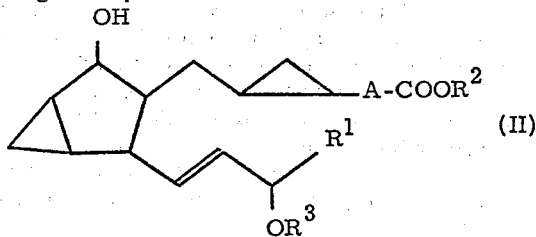

(wherein A and $R^1$ have the meanings already given, $R^2$ represents a hydrogen atom or a carboxyl-protecting group, and $R^3$ represents a hydroxyl-protecting group) to produce a compound having the formula

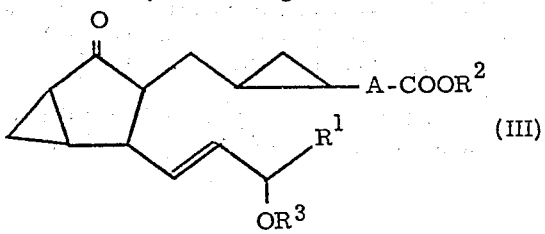

and removing any protecting groups from the compound of formula (III).

When $R^2$ in formula (III) represents a carboxyl-protecting group, this can be removed before, at the same time as, or after the removal of the hydroxyl-protecting group $R^3$. If desired, the resulting acid of formula (I) can be salified by conventional techniques, to produce pharmaceutically acceptable salts thereof, as already described.

In formulae (II) and (III), $R^2$ may be any carboxyl-protecting group which can subsequently be removed so as to leave a free carboxyl group without affecting other parts of the molecule. For example, it may be a straight or branched alkyl group having 1–10 carbon atoms, for instance, methyl, ethyl, n-propyl, isopropyl, n-butyl, isobutyl, n-pentyl, isopentyl, s-amyl, t-amyl, n-hexyl, isohexyl, 2-hexyl, n-heptyl, 3-heptyl, 2-methyl-2-hexyl, n-octyl, 3-methyl-3-heptyl, 2-methyl-2-heptyl, 3-ethyl-3-heptyl, n-nonyl and n-decyl; an unsaturated straight or branched alkyl group having 1 – 11 carbon atoms and having 1 – 5 double and/or triple bonds, for instance, allyl, 1-propenyl, isopropenyl, 1-butenyl, 2-butenyl, 2-methyl-1-propenyl, 2-methyl-2-propenyl, 1-methyl-2-propenyl, 2-pentenyl, 1-methyl-2-butenyl, 1-methyl-1-butenyl, 2-hexenyl, 3-hexenyl, 1-methyl-1-pentenyl, 1-methyl-2-pentenyl, 1,2-dimethyl-1-butenyl, 2-heptenyl, 3-heptenyl, 2-methyl-3-hexenyl, 2-octenyl, 1-butyl-2-butenyl, 2-nonenyl, 3-nonenyl, 3-decenyl, 4-decenyl, 3-undecenyl, 4-undecenyl, 1,3-butadienyl, 1,3-pentadienyl, 1,4-pentadienyl, 1,3-hexadienyl, 1,4-hexadienyl, 2,4-hexadienyl, 1,3-heptadienyl, 1,4-heptadienyl, 2,5-heptadienyl, 1,3-octadienyl, 3,5-nonadienyl, 3,5-decadienyl, 3,5-undecadienyl, 1,3,5-hexatrienyl, 2,4,6-heptatrienyl, 2,4,6-octatrienyl, 2,4,6-nonatrienyl, 3,6,8-decatrienyl, 3,6,8-undecatrienyl, 2-propynyl, 2-butynyl, 2-pentynyl, 2-hexynyl, 2-heptynyl, 2-octynyl, 2-nonynyl, 2-decynyl, 2-undecynyl and 2-penten-4-ynyl; a 5-7 membered cycloalkyl group, i.e. cyclopentyl, cyclohexyl and cycloheptyl; an aryl group which may optionally have 1–3 substituents selected from halogen atoms, straight or branched alkyl groups having 1–5 carbon atoms and straight or branched alkylthio groups having 1–3 carbon atoms, for instance, phenyl, naphthyl, 2-chlorophenyl, 3-chlorophenyl, 4-chlorophenyl, 2,3-dichlorophenyl, 2,4-dichlorophenyl, 2,6-dichlorophenyl, 2,4,6-trichlorophenyl, 2-bromophenyl, 3-bromophenyl, 4-bromophenyl, 2,4-dibromophenyl, 2-iodophenyl, 3-iodophenyl, 4-iodophenyl, 2,4-diiodophenyl, 2-methylphenyl, 3-methylphenyl, 4-methylphenyl, 2-ethylphenyl, 4-n-propylphenyl, 4-n-butylphenyl, 3-isopropylphenyl, 2-isobutylphenyl, 2,3-dimethylphenyl, 2,4-diethylphenyl, 2,4,6-trimethylphenyl, 2-methylthiophenyl, 3-methylthiophenyl, 4-methylthiophenyl, 4-ethylthiophenyl, 4-n-propylthiophenyl and 4-isopropylthiophenyl; a cycloalkyl-substituted alkyl group, consisting of a 5–7 membered cycloalkyl moiety and a straight or branched alkyl moiety having 1–10 carbon atoms, for instance, cyclopentylmethyl, cyclohexylmethyl, cycloheptylmethyl, 2-cyclopentylethyl, 2-cyclohexylethyl, 2-cycloheptylethyl, 3-cyclopentylpropyl, 2-methyl-2-cyclohexylethyl, 2-methyl-2-cycloheptylethyl, 4-cyclopentylbutyl, 5-cyclohexylpentyl, 6-cycloheptylhexyl, 7-cyclopentylheptyl, 8-cyclohexyloctyl, 9-cycloheptylnonyl and 10-cyclopentyldecyl; an aralkyl group consisting of a straight or branched alkyl moiety having 1–5 carbon atoms and an aromatic moiety which may optionally carry 1–3 substituents selected from halogen atoms, straight or branched alkyl groups having 1–5 carbon atoms, hydroxy, amino and phenyl groups, for instance, benzyl, phenethyl, phenylpropyl, phenylbutyl, phenylpentyl, 2-chlorobenzyl, 3-chlorobenzyl, 4-chlorobenzyl, 2,4-dichlorobenzyl, 2,6-dichlorobenzyl, 2,4,6-trichlorobenzyl, 2-bromobenzyl, 3-bromobenzyl, 4-bromobenzyl, 2,4-dibromobenzyl, 2-iodobenzyl, 3-iodobenzyl, 4-iodobenzyl, 2,4-diiodobenzyl, 2-methylbenzyl, 3-methylbenzyl, 4-methylbenzyl, 2-ethylbenzyl, 4-n-propylbenzyl, 4-n-butylbenzyl, 3-isopropylbenzyl, 2-isobutylbenzyl, 2,3-dimethylbenzyl, 2,4-diethylbenzyl, 2,4,6-triethylbenzyl, 2-hydroxybenzyl, 4-hydroxybenzyl, 2,4-dihydroxybenzyl, 2-aminobenzyl, 4-aminobenzyl, 2,4-diaminobenzyl and 4-phenylbenzyl; an ethyl group substituted with 1–3 halogen atoms in the $\beta$-position, for instance, 2,2,2-trichloroethyl, 2,2-dibromoethyl, 2,2,2-tribromoethyl, 2-iodoethyl, 2,2-diiodoethyl and 2,2,2-triiodoethyl; a phenacyl group which may optionally have 1–3 substituents selected from halogen, nitro, straight or branched alkyl groups having 1–3 carbon atoms and straight or branched alkoxy groups having 1–3 carbon atoms, for instance, phenacyl, 4-chlorophenacyl, 4-bromophenacyl, 4-iodophenacyl, 2,4-dichlorophenacyl, 2,4,6-trichlorophenacyl, 2,6-dibromophenacyl, 2-nitrophenacyl, 2,4-dinitrophenacyl, 2,4,6-trinitrophenacyl, 2-methylphenacyl, 2,4-dimethylphenacyl, 2,4,6-trimethylphenacyl, 2-ethylphenacyl, 4-n-propylphenacyl, 2-methoxyphenacyl, 2,4-dimethoxyphenacyl, 2,4,6-trimethoxyphenacyl, 2-ethoxyphenacyl and 4-n-propoxyphenacyl; an oxazolynyl group which may optionally be substituted with 1 or 2 straight or branched alkyl groups having 1–4 carbon atoms together with the carboxyl, for instance, oxazolynyl, 4,4-dimethyloxazolynyl and 4,4-di-n-butyloxazolynyl; or a 5- or 6-membered heterocyclic group containing oxygen or sulphur as hetero-atoms and which may optionally be substituted with 1–3 alkoxy groups having 1–3 carbon atoms, for instance, 2-tetrahydropyranyl, 2-tetrahydrothiopyranyl, 2-tetrahydrothienyl and 4-methoxytetrahydropyran-4-yl; but other protecting groups may also be used.

In formulae (II) and (III), $R^3$ may be any hydroxyl-protecting group which can subsequently be removed so as to leave a free hydroxyl group without affecting any other part of the molecule. For example, it may be a 5- or 6-membered heterocyclic group containing oxygen or sulphur as hetero-atoms and which may optionally be substituted with an alkoxy group having 1–3 carbon atoms, for instance, 2-tetrahydropyranyl, 2-tetrahydrothiopyranyl, 2-tetrahydrothienyl and 4-methoxytetrahydropyran-4-yl; a straight or branched alkyl group having 1–5 carbon atoms, for instance, methyl, ethyl, n-propyl, isopropyl, n-butyl, isobutyl, s-butyl, t-butyl, n-pentyl, isopentyl, s-amyl and t-amyl; a straight or branched alkoxyalkyl group having 1–5 carbon atoms each in the alkyl and alkoxy moieties, for instance, methoxymethyl, ethoxymethyl, n-propoxymethyl, isopropoxymethyl, n-butoxymethyl, isobutoxymethyl, s-butoxymethyl, n-pentoxymethyl, isopentoxymethyl, s-amyloxymethyl, 1-ethoxyethyl, 1-ethoxypropyl, 1-ethoxybutyl, 2-ethoxybutyl, 1-ethoxypentyl and 2-ethoxy-3-methylpentyl; a 5–7 membered cycloalkyl group substituted with a straight or branched alkoxy group having 1–5 carbon atoms, for instance, 1-methoxycyclopentyl, 1-ethoxycyclopentyl, 1-n-propoxycyclopentyl, 1-methoxycyclohexyl, 1-ethoxycyclohexyl, 1-n-propoxycyclohexyl, 1-isopropoxycyclohexyl, 1-n-butoxycyclohexyl, 1-isobutoxycyclohexyl, 1-n-pentoxycyclohexyl, 1-s-amyloxycyclohexyl, 4-methoxycyclohexyl, 4-ethoxycyclohexyl, 1-methoxycycloheptyl, 1-ethoxycycloheptyl, 1-n-propoxycycloheptyl, 1-n-butoxycycloheptyl and 1-n-pentoxycycloheptyl; a straight or branched trialkylsilyl group having 1–5 carbon atoms, for instance, trimethylsilyl, triethylsily, tri-n-propylsilyl, triisopropylsilyl, tri-n-butylsilyl, triisobutylsilyl and tri-n-pentylsilyl; an ester residue having the formula $R^4OCO$- wherein $R^4$ represents a straight or branched alkyl group having 1–5 carbon atoms such as methyl, ethyl, n-propyl, isopropyl, n-butyl, isobutyl and n-pentyl; an ethyl group substituted with 1–3 halogen atoms in the $\beta$-position, for instance, 2,2,2-trichloroethyl, 2,2-dibromoethyl, 2,2,2-tribromoethyl, 2-iodoethyl, 2,2-diiodoethyl and 2,2,2-triiodoethyl; a phenyl group which may optionally carry 1–3 substituents selected from nitro, halogen and phenyl, for instance, phenyl, 2-nitrophenyl, 4-nitrophenyl, 2-chlorophenyl, 4-chlorophenyl, 2-bromophenyl, 4-bromophenyl, 2,4-dichlorophenyl, 2,4,6-trichlorophenyl and biphenylyl; a 5- or 6-membered cycloalkyl group which may optionally carry 1–3 substituents selected from halogen atoms and straight or branched alkyl groups having 1–5 carbon atoms, for instance, cyclopentyl, cyclohexyl, 2-chlorocyclopentyl, 3-chlorocyclopentyl, 2,4-dichlorocyclopentyl, 2,3,5-trichlorocyclopentyl, 2-bromocyclopentyl, 3-iodocyclopentyl, 2-chlorocyclohexyl, 4-chlorocyclohexyl, 2,4-dichlorocyclohexyl, 2,4,6-trichlorocyclohexyl, 2-bromocyclohexyl, 4-iodocyclohexyl, 2-methylcyclopentyl, 3-ethylcyclopentyl, 2-n-propylcyclopentyl, 3-n-butylcyclopentyl, 3-n-pentylcyclopentyl, 2-methylcyclohexyl, 2-ethylcyclohexyl, 2-n-propylcyclohexyl, 4-isopropylcyclohexyl, 2-n-butylcyclohexyl, 4-isobutylcyclohexyl, 2-n-pentylcyclohexyl, 4-isopentylcyclohexyl, 2,4-dimethylcyclohexyl and 2,4,6-trimethylcyclohexyl; an aralkyl group consisting of a straight or branched alkyl moiety of 1–5 carbon atoms and an aromatic moiety which may optionally carry 1–3 substituents selected from nitro, halogen and phenyl, for instance, benzyl, phenethyl, phenylpropyl, phenylbutyl, phenylpentyl, 4-nitrobenzyl, 4-nitrophenethyl, 2-chlorobenzyl, 4-chlorophenethyl, 2-bromobenzyl, 4-bromophenethyl, (2,4-dichlorophenyl)propyl, (2,4,6-trichlorophenyl)butyl, 4-phenylbenzyl and 4-phenylphenethyl; a cycloalkyl-substituted alkyl group consisting of a straight or branched alkyl moiety of 1–5 carbon atoms and a 5- or 6-membered cycloalkyl moiety which may optionally carry 1–3 substituents selected from halogen atoms and straight or branched alkyl groups having 1–5 carbon atoms, for instance cyclopentylmethyl, 2-cyclopentylethyl, 3-cyclopentylpropyl, 4-cyclopentylbutyl, 5-cyclopentylpentyl, cyclohexylmethyl, 2-cyclohexylethyl, 3-cyclohexylpropyl, 4-cyclohexylbutyl, 5-cyclohexylpentyl, (2-chlorocyclopentyl)methyl, (3-chlorocyclopentyl)methyl, 2-(2,4-dichlorocyclopentyl)ethyl, 2-(2-bromocyclopentyl)ethyl, 2-(3-iodocyclopentyl)ethyl, (2-chlorocyclohexyl)methyl, (4-chlorocyclohexyl)methyl, (2,4-dichlorocyclohexyl)methyl, 2-(2,4,6-trichlorocyclohexyl)ethyl, 2-(2-bromocyclohexyl)ethyl, 2-(2-iodocyclohexyl)ethyl, (2-methylcyclopentyl)methyl, (3-ethylcyclopentyl)methyl, 2-(3-n-propylcyclopentyl)ethyl, 3-(2-n-butylcyclopentyl)propyl, (2-methylcyclohexyl)methyl, (4-methylcyclohexyl)methyl, (2,4-dimethylcyclohexyl)methyl, 2-(4-n-propylcyclohexyl)ethyl, 3-(2-methylcyclohexyl)propyl and 3-(4-n-butylcyclohexyl)propyl; an acyl group having the formula $R^5CO$- wherein $R^5$ represents a straight or branched alkyl group of 1–10 carbon atoms which may optionally be substituted with 1–3 halogen atoms such as methyl, ethyl, n-propyl, isopropyl, n-butyl, s-butyl, t- butyl, n-pentyl, n-hexyl, n-heptyl, n-octyl, n-nonyl, n-decyl, 2,2,2-trichloroethyl and 2,2,2-trifluoroethyl; an aryl group which may optionally carry 1–3 substituents selected from halogen atoms, straight or branched alkyl groups having 1–5 carbon atoms, nitro, hydroxy, amino and phenyl, for instance, phenyl, 2-chlorophenyl, 3-chlorophenyl, 4-chlorophenyl, 2,4-dichlorophenyl, 2,6-dichlorophenyl, 2,4,6-trichlorophenyl, 2-bromophenyl, 4-bromophenyl, 2,4-dibromophenyl, 2-methylphenyl, 3-methylphenyl, 4-methylphenyl, 2-ethylphenyl, 4-n-propylphenyl, 4-n-butylphenyl, 3-isopropylphenyl, 2-isobutylphenyl, 2,4-dimethylphenyl, 2,4-diethylphenyl, 2,4,6-trimethylphenyl, 2-n-pentylphenyl, 2-nitrophenyl, 2,4-dinitrophenyl, 2,4,6-trinitrophenyl, 2-hydroxyphenyl, 2,4-dihydroxyphenyl, 2-aminophenyl, 2,4-diaminophenyl and biphenylyl; an aralkyl group consisting of a straight or branched alkyl moiety of 1–5 carbon atoms and an aromatic moiety which may optionally carry 1–3 substituents selected from halogen atoms, straight or branched alkyl groups having 1–5 carbon atoms, nitro, hydroxy, amino and phenyl, for instance, benzyl, phenethyl, phenylpropyl, phenylbutyl, phenylpentyl, 2-chlorobenzyl, 3-chlorobenzyl, 4-chlorobenzyl, 2,4-dichlorobenzyl, 2,6-dichlorobenzyl, 2,4,6-trichlorobenzyl, 2-bromobenzyl, 4-bromobenzyl, 2,4-dibromobenzyl, 2-chlorophenethyl, 3-chlorophenethyl, 4-chlorophenethyl, 2,4-dichlorophenethyl, 2,6-dichlorophenethyl, 2,4,6-trichlorophenethyl, 2-bromophenethyl, 4-bromophenethyl, 2,4-dibromophenethyl, 2-methylbenzyl, 3-methylbenzyl, 4-methylbenzyl, 2-ethylbenzyl, 4-n-propylbenzyl, 4-n-butylbenzyl, 3-isopropylbenzyl, 2-isobutylbenzyl, 2,4-dimethylbenzyl, 2,4-diethylbenzyl, 2,4,6-trimethylbenzyl, 2-n-pentylbenzyl, 2-methylphenethyl, 3-methylphenethyl, 4-methylphenethyl, 2-ethylphenethyl, 4-n-propylphenethyl, 4-n-butylphenethyl, 4-n-pentylphenethyl, 2-nitrobenzyl, 2,4-dinitrobenzyl, 2,4,6-trinitrobenzyl, 2-nitrophenethyl, 2,4-dinitrophenethyl, 2,4,6-trinitrophenethyl, 2-hydroxybenzyl, 2,4-dihydroxybenzyl, 2-hydroxyphenethyl, 2,4-dihydroxyphenethyl, 2-aminobenzyl, 2,4-diaminobenzyl, 2-aminophenethyl, 2,4-diaminophenethyl, 4-phenylbenzyl and 4-phenylphenethyl; a 5–7 membered cycloalkyl group which may optionally carry 1–3 substituents selected from halogen atoms, straight or branched alkyl groups having 1–5 carbon atoms, nitro, hydroxy, amino and phenyl, for instance, cyclopentyl, cyclohexyl, cycloheptyl, 2-chlorocyclopentyl, 2-chlorocyclohexyl, 2-chlorocycloheptyl, 4-chlorocyclohexyl, 4-chlorocycloheptyl, 2,4-dichlorocyclopentyl, 2,4-dichlorocyclohexyl, 2,6-dichlorocycloheptyl, 2,3,5-trichlorocyclopentyl, 2,4,6-trichlorocyclohexyl, 2-bromocyclopentyl, 2-bromocyclohexyl, 2-bromocycloheptyl, 4-bromocyclohexyl, 4-bromocycloheptyl, 2,4-dibromocyclopentyl, 2,4-dibromocyclohexyl, 2-methylcyclopentyl, 2-methylcyclohexyl, 2-methylcycloheptyl, 3-methylcyclopentyl, 3-methylcyclohexyl, 4-methylcyclohexyl, 4-methylcycloheptyl, 2-ethylcyclopentyl, 2-ethylcyclohexyl, 4-n-propylcyclohexyl, 4-n-propylcycloheptyl, 3-n-butylcyclopentyl, 4-n-butylcyclohexyl, 3-isopropylcyclohexyl, 2-isobutylcyclohexyl, 2,4-dimethylcyclopentyl, 2,4-dimethylcyclohexyl, 2,4-dimethylcycloheptyl, 2,4-diethylcyclopentyl, 2,4-diethylcyclohexyl, 2,3,5-trimethylcyclopentyl, 2,4,6-trimethylcyclohexyl, 2,4,6-trimethylcycloheptyl, 2-n-pentylcyclohexyl, 2-nitrocyclopentyl, 2-nitrocyclohexyl, 3-nitrocycloheptyl, 2,4-dinitrocyclohexyl, 2,4,6-trinitrocyclohexyl, 2-hydroxycyclopentyl, 2-hydroxycyclohexyl, 4-hydroxycycloheptyl, 2,4-dihydroxycyclohexyl, 2,4,6-trihydroxycyclohexyl, 2-aminocyclopentyl, 2-aminocyclohexyl, 4-aminocycloheptyl, 2,4-diaminocyclohexyl, 2,4,6-triaminocyclohexyl and 4-phenylcyclohexyl; or a cycloalkyl-substituted alkyl group consisting of a straight or branched alkyl moiety of 1–10 carbon atoms and a 5–7 membered cycloalkyl moiety which may optionally carry 1–3 substituents selected from halogen atoms, straight or branched alkyl groups having 1–5 carbon atoms, nitro, hydroxy, amino and phenyl, for instance, cyclopentylmethyl, 2-cyclopentylethyl, 3-cyclopentylpropyl, 4-cyclopentylbutyl, cyclohexylmethyl, 2-cyclohexylethyl, 3-cyclohexylpropyl, 4-cyclohexylbutyl, 5-cyclohexylpentyl, 6-cyclohexylhexyl, 7-cyclohexylheptyl, 8-cyclohexyloctyl, 9-cyclohexylnonyl, 10-cyclohexyldecyl, cycloheptylmethyl, 2-cycloheptylethyl, 3-cycloheptylpropyl, 4-cycloheptylbutyl, 2-chlorocyclopentylmethyl, 2-chlorocyclohexylmethyl, 2-(2-chlorocyclohexyl)ethyl, 2-chlorocycloheptylmethyl, 4-chlorocyclohexylmethyl, 2-(4-chlorocyclohexyl)ethyl, 4-chlorocycloheptylmethyl, 2,4-dichlorocyclohexylmethyl, 2,6-dichlorocyclohexylmethyl, 2-(2,6-dichlorocyclohexyl)ethyl, 2,4,6-trichlorocyclohexylmethyl, 2-bromocyclopentylmethyl, 2-bromocyclohexylmethyl, 2-(2-bromocyclohexyl)ethyl, 2-bromocycloheptylmethyl, 4-bromocyclohexylmethyl, 2,4-dibromocyclohexylmethyl, 2-methylcyclohexylmethyl, 2-(2-methylcyclohexyl)ethyl, 3-methylcyclopentylmethyl, 4-methylcyclohexylmethyl, 2-(2-ethylcyclohexyl)ethyl, 3-(4-n-propylcyclohexyl)propyl, 4-(4-n-butylcyclohexyl)butyl, 2,4-dimethylcyclohexylmethyl, 2,4-diethylcyclohexylmethyl, 2,4,6-trimethylcyclohexylmethyl, 2-nitrocyclopentylmethyl, 2-nitrocyclohexylmethyl, 2-(2-nitrocyclohexyl)ethyl, 4-nitrocyclohexylmethyl, 4-nitrocycloheptylmethyl, 2-(2,4-dinitrocyclohexyl)ethyl, 3-(2,4,6-trinitrocyclohexyl)propyl, 2-hydroxycyclopentylmethyl, 2-hydroxycyclohexylmethyl, 2,4-dihydroxycyclohexylmethyl, 2,4,6-trihydroxycyclohexylmethyl, 2-hydroxycycloheptylmethyl, 2-aminocyclopentylmethyl, 2-aminocyclohexylmethyl, 2,4-diaminocyclohexylmethyl, 2,4,6-triaminocyclohexylmethyl, 2-aminocycloheptylmethyl and 4-phenylcyclohexylmethyl; but other protecting groups may also be used.

In the first step of the process of the invention, the compound of formula (III) is produced by treating the compound of formula (II) with an oxidizing agent, optionally in the presence of a solvent. Preferred examples of oxidizing agents are those of the chromic acid type, such as chromic anhydride, chromic anhydride/pyridine complex (Collins reagent), chromic anhydride/aqueous sulphuric acid (Jones reagent), sodium dichromate or potassium dichromate; organic active halogen compounds, such as N-bromoacetamide, N-bromosuccinimide, N-bromophthalimide, N-chloro-p-toluenesulphonamide and N-chlorobenzenesulphonamide; aluminium aloxides, such as aluminium t-butoxide and aluminium isopropoxide; dimethylsulphoxide/dicyclohexylcarbodiimide; and dimethylsulphoxide/acetic anhydride.

If a solvent is employed, its choice is not particularly critical, so long as it is inert to the reaction. When using oxidizing agents of the chromic acid type, the preferred solvents are organic acids and mixtures of organic acids with organic anhydrides (e.g. acetic acid, or acetic acid/acetic anhydride), or halogenated hydrocarbons (e.g. dichloromethane, chloroform or carbon tetrachloride). When using organic active halogen compounds as oxidizing agents, aqueous organic solvents are preferred, such as aqueous t-butanol, aqueous acetone or aqueous pyridine. When using aluminium alkoxides as the oxidizing agents, the preferred reaction solvents are aromatic hydrocarbons (e.g. benzene, toluene or xylene), and the reaction is also preferably performed in the presence of an excess of a hydrogen acceptor (e.g. a ketone, such as acetone, methyl ethyl ketone, cyclohexanone or benzoquinone); the reaction system should also be completely free from water. If the oxidizing agent is dimethylsulphoxide/dicyclohexylcarbodiimide or dimethylsulphoxide/acetic anhydride, an excess of the dimethylsulphoxide can be used as solvent, no other solvent generally being needed; and, when dimethylsulphoxide/dicyclohexylcarbodiimide is employed, it is preferred to add a catalytic amount of an acid (e.g. phosphoric or acetic acid), in the conventional manner.

The preferred oxidizing agents are those of the chromic acid type, especially chromic anhydride/pyridine complex (Collins reagent) and chromic anhydride/aqueous sulphuric acid (Jones reagent).

The reaction temperature is not particularly critical, but it is preferred to perform the oxidation at a relatively low temperature, so as to suppress side-reactions. Temperatures from $-20°C$ to room temperature are generally suitable, and those from $0°C$ to room temperature are preferred. The reaction time will depend on the reaction temperature and the type of oxidizing agent employed, but it is generally from about 10 minutes to 1 hour.

After completion of the reaction, the product of formula (III) can be recovered from the reaction mixture by conventional techniques. For example, an organic solvent such as ether is added to the reaction mixture, insolubles are removed, the organic phase is washed and dried, and the solvent is evaporated off, leaving the compound of formula (III). If necessary, the product thus obtained can be further purified by conventional techniques, for example by column chromatography or thin-layer chromatography.

The hydroxyl-protecting group $R^3$ and, when appropriate, also the carboxyl-protecting group $R^2$ can be removed from the compound of formula (III) by conventional techniques appropriate to the nature of these protecting groups.

Thus, when the hydroxyl-protecting group is a heterocyclic group such as 2-tetrahydropyranyl, an alkoxyalkyl group such as methoxymethyl, or an alkoxycycloalkyl group such as 1-methoxycyclohexyl, it can readily be removed by treating the compound of formula (III) with an acid, for example an organic acid such as formic, acetic, propionic, butyric, oxalic or malonic acid, or a mineral acid such as hydrochloric, hydrobromic or sulphuric acid. The reaction can be carried out in the absence of any solvent, but the presence of a solvent is preferred because the reaction then proceeds more smoothly. The choice of solvent is not critical, provided that it is inert to the reaction; but preferred solvents are water, alcohols such as methanol and ethanol, ethers such as tetrahydrofuran and dioxane, and mixtures of such organic solvents with water. The reaction temperature is not particularly critical, and may suitably be between room temperature and the reflux temperature of the solvent, if one is employed.

If the hydroxyl-protecting group is an alkyl group such as methyl, it can readily be removed by treating the compound of formula (III) with a boron halide, such as boron trichloride or boron tribromide. The reaction can be carried out in the absence of any solvent, but the presence of a solvent is preferred because the reaction then proceeds more smoothly. The choice of solvent is not critical, provided that it is inert to the reaction, but halogenated hydrocarbons such as dichloromethane and chloroform are preferred. The reaction temperature is also not particularly critical, but it is desirable to use a relatively low temperature in order to suppress side-reactions, and temperatures between $-30°C$ and room temperature are preferred.

If the hydroxyl-protecting group is a trialkylsilyl group such as trimethylsilyl, it can readily be removed by treating the compound of formula (III) with water, or with an aqueous acid or base. There are no particular limits on the choice of the acid or base. For instance, the acid may be an organic acid, such as formic, acetic, propionic, butyric, oxalic or malonic acid, or a mineral acid, such as hydrochloric, hydrobromic or sulphuric acid; and the base may be an alkali or alkaline earth metal hydroxide or carbonate, such as potassium hydroxide, calcium hydroxide, potassium carbonate or calcium carbonate. When water is employed in this step, no other solvent is necessary; but, if an additional solvent is employed, it may suitably be a mixture of water with an organic solvent, for example an ether such as tetrahydrofuran or dioxane, or an alcohol such as methanol or ethanol. The reaction temperature is not particularly critical, but it is generally convenient to perform the reaction at around room temperature.

If the hydroxyl-protecting group is a carbonic ester residue such as ethoxycarbonyl, or an acyl group such as acetyl, it can readily be removed by treating the compound of formula (III) with an acid or base. Examples of preferred acids and bases are mineral acids, such as hydrochloric, hydrobromic and sulphuric acid, and alkali or alkaline earth metal hydroxides and carbonates, such as sodium hydroxide, potassium hydroxide, calcium hydroxide, sodium carbonate, potassium carbonate and calcium carbonate. It is generally most convenient to perform the reaction under basic conditions. The reaction can be carried out without any solvent, but the presence of a solvent is preferred since the reaction then proceeds more smoothly. There are no particular limits on the choice of solvent, so long as it is inert to the reaction, but preferred examples are water, alcohols such as methanol and ethanol, ethers such as tetrahydrofuran and dioxane, or mixtures of such organic solvents with water. The reaction temperature is also not particularly critical, but it is preferred to operate at between room temperature and the reflux temperature of the solvent (if one is employed), and can vary with the nature of the protecting group to be removed.

After removal of the hydroxyl-protecting groups, the desired product can be recovered from the reaction mixture by conventional techniques. For example, the reaction mixture is neutralized and extracted with an organic solvent, and the solvent is evaporated off from the extract to leave the desired product. If necessary, the product thus obtained can be further purified by conventional means, such as column chromatography or thin-layer chromatography.

When $R^2$ in formula (III) represents a carboxyl-protecting group, it can be removed by conventional techniques suited to the nature of this protecting group.

Thus, if the carboxyl-protecting group is a hydrocarbon group (e.g. an alkyl group such as methyl, an unsaturated aliphatic group such as allyl, a cycloalkyl group such as cyclohexyl, an aryl or substituted aryl group such as phenyl, a cycloalkyl-substituted alkyl group such as cyclohexylmethyl, or an aralkyl or substituted aralkyl group such as benzyl), it can readily be removed by treatment with an acid or a base. The acid or base may be any of those used in conventional hydrolysis, for example a mineral acid such as hydrochloric, hydrobromic or sulphuric acid, or an alkali or alkaline earth metal hydroxide or carbonate such as sodium hydroxide, potassium hydroxide, barium hydroxide, sodium carbonate, potassium carbonate, or calcium carbonate. It is generally most convenient to perform the reaction under basic conditions. The reaction can be carried out without any solvent, but the presence of a solvent is preferred since the reaction then proceeds more smoothly. There are no particular limits on the choice of solvent, so long as it is inert to the reaction, but preferred examples are water, and mixtures of water with alcohols such as methanol and ethanol or with ethers such as tetrahydrofuran and dioxane. The reaction temperature is not particularly critical, but it is preferred to operate at between room temperature and the reflux temperature of the solvent, if one is employed.

If the carboxyl-protecting group is an aralkyl group such as benzyl, it can also be removed by catalytic reduction, using a catalyst such as platinum oxide or palladium on carbon.

If the carboxyl-protecting group is a haloalkyl group such as 2,2,2-trichloroethyl, it can readily be removed by treatment with zinc and acetic acid, optionally in the presence of a solvent. There are no particular limits on the choice of solvent, so long as it is inert to the reaction, but preferred examples are water, ethers such as tetrahydrofuran and dioxane, alcohols such as methanol and ethanol, and mixtures of such organic solvents with water. The reaction temperature is not particularly critical, but it is generally preferred to operate at about room temperature.

If the carboxyl-protecting group is a phenacyl or substituted phenacyl group, it can be removed by treatment with an acid as in the case of the hydrocarbon protecting groups, with chlorine, or with zinc and acetic acid as in the case of the haloalkyl groups.

If the carboxyl-protecting group is an oxazolynyl group such as 4,4-dimethyloxazolynyl, it can be removed by treatment with an acid, preferably a mineral acid such as hydrochloric, sulphuric or perchloric acid. It is generally preferred to carry out this reaction in the presence of water. The reaction can be carried out in the absence of any solvent, but the presence of a solvent is preferred because the reaction then proceeds more smoothly. The choice of solvent is not critical, provided that it is inert to the reaction. Apart from water, preferred solvents are mixtures of water with an organic solvent, for example an alcohol such as methanol or ethanol, an ether such as tetrahydrofuran or dioxane, or an organic acid such as acetic acid. The reaction temperature is also not particularly critical, but it is generally preferred to operate at from room temperature to 100°C.

If the carboxyl-protecting group is a heterocyclic group such as 2-tetrahydropyranyl, it can be removed by treatment with an acid. Examples of preferred acids are organic acids, such as formic, acetic, propionic, butyric, oxalic and malonic acid, and mineral acids, such as hydrochloric, hydrobromic and sulphuric acid. The reaction can be carried out without any solvent, but the presence of a solvent is preferred since the reaction then proceeds more smoothly. There are no particular limits on the choice of solvent, so long as it is inert to the reaction, but preferred examples are water, alcohols such as methanol and ethanol, ethers such as tetrahydrofuran and dioxane, and mixtures of such organic solvents with water. The reaction temperature is not particularly critical, but it is preferred to operate at from room temperature to the reflux temperature of the solvent (if one is employed), especially at about room temperature. The reaction time depends on the type of protecting group to be removed and the reaction conditions.

When the removal of the carboxyl-protecting group is conducted under basic conditions, the configuration of the branched chain containing the carboxyl group which is attached to the five-membered ring changes from α-configuration to β-configuration, under the influence of the three-membered ring fused with the five-membered ring.

After completion of the reaction for removing the carboxyl-protecting group, the desired reaction product can be recovered from the reaction mixture by conventional techniques. For example, the reaction mixture is extracted with an organic solvent, and the solvent is evaporated off to leave the desired product. If necessary, the product thus obtained can be further purified by conventional means, such as column chromatography or thin-layer chromatography.

If desired, the compound of formula (I) thus obtained can be salified, in the conventional manner. Also, the various geometrical and/or optical isomers of the compound of formula (I) can be isolated or resolved at an appropriate stage in the synthesis.

The starting materials of formula (II) used in the process of the invention are new compounds and can be prepared by the process shown in the following reaction scheme:

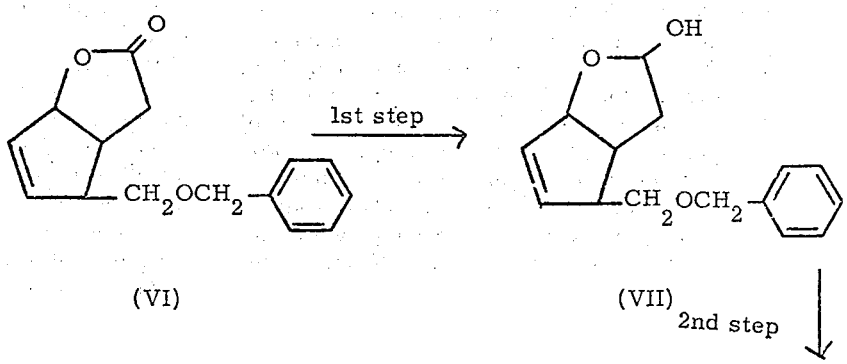

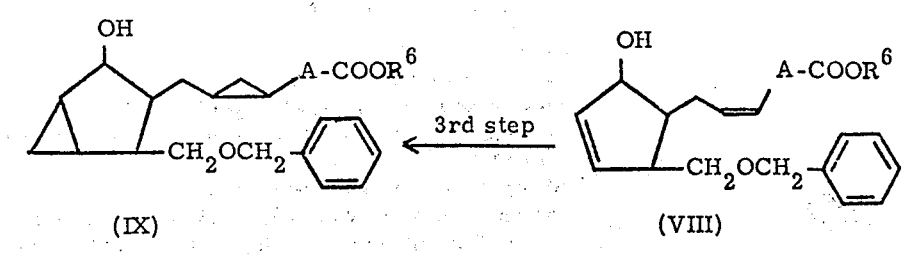
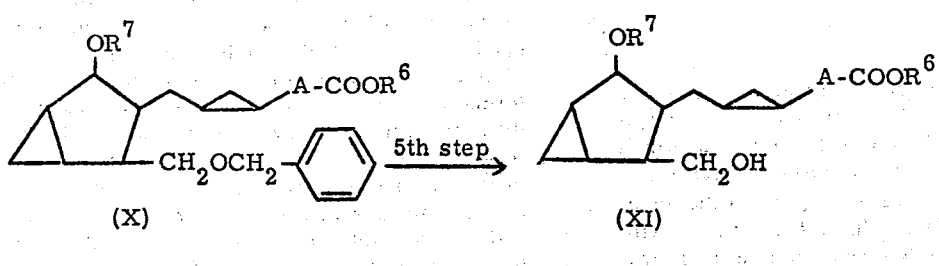
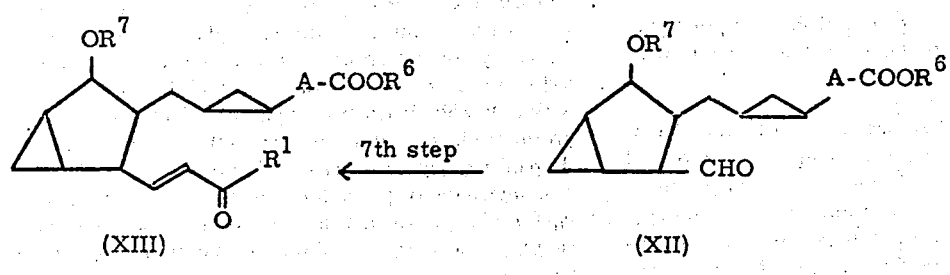
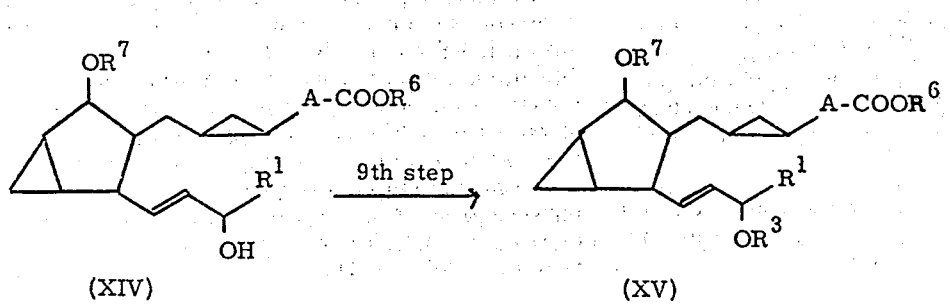

10th step

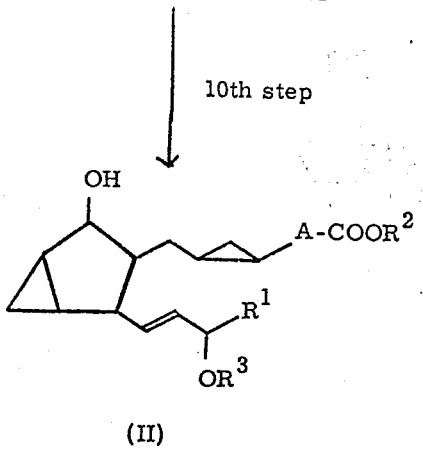

(II)

In the reaction scheme, A, $R^1$, $R^2$ and $R^3$ have the meanings already given. $R^6$ represents a carboxyl-protecting group: it may be any protecting group which can subsequently be removed so as to leave a free carboxyl group without affecting other parts of the molecule, for example one of those listed hereinbefore with reference to group $R^2$. $R^7$ represents a hydroxyl-protecting group, and may be any protecting group which can subsequently be removed to leave a free hydroxyl group without affecting other parts of the molecule, for example one of those listed hereinbefore with reference to group $R^3$; but the protecting groups must be selected so that $R^3$ is not removed along with $R^7$ during the tenth reaction step.

The process for the preparation of the compounds of formula (II), shown in the reaction scheme, will now be described in greater detail.

In the reaction of the first step, the compound (VI) is treated with a reducing agent, giving the compound (VII). Examples of preferred reducing agents are metal hydrides, such as diisobutylaluminium hydride, sodium borohydride, potassium borohydride, lithium borohydride, tri-t-butoxylithium aluminium hydride and trimethoxylithium aluminium hydride. It is preferred to use diisobutylaluminium hydride, because the reaction then proceeds smoothly at a relatively low temperature and without side-reactions. The reduction can be performed without using any solvent, but the presence of a solvent is preferred since the reaction then proceeds more smoothly. There are no particular limits on the choice of solvent, so long as it is inert to the reaction, but it is preferred to use an alcohol such as methanol or ethanol, an ether such as tetrahydrofuran or dioxane, or a hydrocarbon such as benzene or toluene. The reduction is desirably carried out at a low temperature, so as to avoid side-reactions, preferably at from −75°C to room temperature.

In the second step of the reaction scheme, the compound (VIII) is prepared by reacting the compound (VII) with a Wittig reagent of formula $$(R^8)_3P^+—C^-H—A—COOM \quad (XVI)$$

wherein:
A has the meaning already given;
$R^8$ represents a hydrocarbon group, for instance an aryl group (e.g. phenyl) or an alkyl group (e.g. n-butyl); and
M represents an alkali metal (e.g. sodium or potassium); acidifying the product of the reaction, so as to convert it into the free acid, and protecting the carboxyl group of the resulting product. It is preferred to use a stoichiometric excess of the Wittig reagent (XVI), and generally between 1 and 20 moles of the Wittig reagent are used per mole of the compound (VII). The Wittig reaction is usually performed in a solvent, which may be any of those conventionally used for Wittig reactions, for example an ether such as diethyl ether, tetrahydrofuran or dioxane, a hydrocarbon such as benzene, toluene or hexane, a dialkylsulphoxide such as dimethylsulphoxide, a dialkylformamide such as dimethylformamide, or a halogenated hydrocarbon such as dichloromethane or chloroform. Preferably, the reaction is performed under an atmosphere of an inert gas, such as nitrogen, argon or helium. The reaction temperature is not particularly critical, and may generally be between 0°C and the reflux temperature of the solvent, preferably about room temperature.

The product of the Wittig reaction is a salt, which is readily converted into the free acid by treatment with an organic acid, such as acetic, propionic or oxalic acid, or with a mineral acid, such as hydrochloric or hydrobromic acid. The resulting product is then treated with a carboxyl-protecting agent, suitably one which will provide a carboxyl-protecting group such as alkyl (e.g. methyl), an unsaturated aliphatic group (e.g. allyl), a cycloalkyl group (e.g. cyclohexyl) or a cycloalkyl-substituted alkyl group (e.g. cyclohexylmethyl), or with a diazohydrocarbon capable of forming an aralkyl group such as benzyl, for example diazomethane, 1-diazo-2-propene, diazocyclohexane, cyclohexyldiazomethane or phenyldiazomethane. This reaction is preferably performed in the presence of a solvent: there are no particular limits on the choice of solvent, so long as it is inert to the reaction, but it is preferably an ether such as diethyl ether or dioxane. The reaction temperature is not particularly critical, but it is preferred to use a relatively low temperature so as to suppress side-reactions and avoid decomposing the diazohydrocarbon when one is used as the protecting agent. Usually, it is preferred to perform the reaction under ice-cooling.

The free carboxyl group can also be protected with an aryl or substituted aryl group (e.g. phenyl), by using a phenol or derivative thereof as the protecting agent. This reaction is carried out in the presence of an acid, preferably a mineral acid such as hydrochloric, hydrobromic or sulphuric acid, optionally in the presence of a solvent. If a solvent is employed, there are no particular limits on its choice, so long as it is inert to the reaction, but it is suitably an ether such as diethyl ether, dioxane or tetrahydrofuran, or a hydrocarbon such as benzene or toluene. The reaction temperature is also not particularly critical, but is usually from room temperature to the reflux temperature of the solvent, if one is employed.

Another carboxyl-protecting group which can be used is a halogenated ethyl group (e.g. 2,2,2-trichloroethyl), in which case the protecting agent employed is the appropriate halogenated ethanol (e.g. 2,2,2-trichloroethanol). This reaction is preferably carried out in the presence of a dehydrating agent, such as sulphuric acid or dicyclohexylcarbodiimide. The reaction can be performed without any separate solvent, but the presence of a solvent is preferred since the reaction then proceeds more smoothly. There are no particular limits on the choice of solvent, so long as it is inert to the reaction, but it is preferred to use an ether such as diethyl ether or dioxane. The reaction temperature is not particularly critical, but it is preferred to operate at about room temperature.

Another carboxyl-protecting group which can be employed is phenacyl or substituted phenacyl, in which case the protecting reagent is an optionally substituted halogenated phenacyl, such as bromophenacyl. In this case, the reaction is performed on an alkali metal salt (e.g. the sodium or potassium salt) of the product of the Wittig reaction, rather than on the free acid. The reaction is preferably carried out in the presence of a solvent, for example an ether such as dioxane or tetrahydrofuran, a dialkylformamide such as dimethylformamide, or a dialkylsulphoxide such as dimethylsulphoxide. The reaction temperature is not particularly critical, and may suitably be from room temperature to the reflux temperature of the solvent, if one is employed.

Yet another kind of carboxyl-protecting reagent which can be used is a 2-aminoethanol derivative such as 2-amino-2-methyl-1-propanol, which will form an oxazolynyl group (e.g. 4,4-dimethyloxazolynyl) together with the carboxyl. This reaction is optionally performed in the presence of a solvent. If a solvent is used, there are no particular limits on its choice, so long as it is inert to the reaction, suitable examples being an ether such as dioxane or tetrahydrofuran, or a hydrocarbon such as benzene or toluene. The reaction temperature is not particularly critical, but it is generally preferred to carry out the reaction at the reflux temperature of the solvent, if one is employed.

A still further type of carboxyl-protecting reagent which can be used is a heterocyclic compound such as dihydropyran, forming a heterocyclic protecting group such as 2-tetrahydropyranyl. This protecting reaction is carried out in the presence of a small amount of an acid, for example a mineral acid such as hydrochloric or hydrobromic acid, or an organic acid such as picric, trifluoroacetic, benzenesulphonic or p-toluenesulphonic acid. The reaction can be performed without any solvent, but the presence of a solvent is preferred since the reaction then proceeds more smoothly. There are no particular limits on the choice of solvent, so long as it is inert to the reaction, but it is preferably a halogenated hydrocarbon such as chloroform or dichloromethane, or a nitrile such as acetonitrile. The reaction temperature is also not particularly critical, and may suitably be from room temperature to the reflux temperature of the solvent, if one is employed, most preferably at about room temperature.

In the third step of the reaction scheme, the two double bonds in compound (VIII) are converted into three-membered rings, giving the compound (IX). The reaction can be brought about by treating the compound (VIII) with one of the reagents conventionally used for forming a three-membered ring from a double bond, for example a zinc/methylene dihalide reagent such as diethylzinc/methylene iodide, zinc powder/copper chloride/methylene iodide, zinc/copper/methylene iodide (Simmons-Smith reagent) and zinc (granules or powder)/acetoxy silver/methylene iodide, a diazomethane/zinc halide reagent such as diazomethane/zinc iodide, benzylmethylmercury iodide, or a dialkylmethylaluminium iodide reagent such as diethylmethylaluminium iodide. The reaction can be carried out without any separate solvent, but the presence of a solvent is preferred since the reaction then proceeds more smoothly. Preferred solvents are ethers such as diethyl ether and isopropyl ether, and hydrocarbons such as n-hexane, cyclohexane and benzene. The reaction temperature is not particularly critical, and the reaction can be carried out under ice-cooling or at a temperature up to the reflux temperature of the solvent, if one is employed.

In the fourth step, the hydroxyl group of the compound (IX) is protected, to give the compound (X). This reaction is performed by treating the compound (IX) with a hydroxyl-protecting agent of conventional type.

Thus, if the hydroxyl-protecting group is to be a heterocyclic group such as 2-tetrahydropyranyl, the compound (IX) is treated with a heterocyclic compound such as dihydropyran. If the protecting group is to be an alkoxycycloalkyl group, for example 1-methoxycyclohexyl, then the protecting agent used is an alkoxycycloalkene, for example methoxy-1-cyclohexene. In such cases, the reaction is suitably performed in the presence of a small amount of an acid, for instance a mineral acid such as hydrochloric or hydrobromic acid, or an organic acid such as picric, trifluoroacetic, benzenesulphonic or p-toluenesulphonic acid. The reaction can be carried out without any separate solvent, but the presence of a solvent is preferred, since the reaction then proceeds more smoothly. There are no particular limits on the choice of solvent, so long as it is inert to the reaction, but it is preferably a hydrocarbon such as benzene or toluene, a halogenated hydrocarbon such as chloroform or dichloromethane, or a nitrile such as acetonitrile. The reaction temperature is also not particularly critical, being suitably from room temperature to the reflux temperature of the solvent, but it is generally preferred to operate at about room temperature.

If the hydroxyl-protecting group is to be a hydrocarbon group such as methyl, the compound (IX) is treated with a halogenated hydrocarbon protecting agent such as methyl chloride. If the protecting group is to be an alkoxyalkyl group, for example methoxymethyl, an alkoxy-substituted halogenated hydrocarbon is used, such as methoxymethylene chloride. If the protecting group is to be a trialkylsilyl group such as trimethylsilyl, then the compound (IX) is treated with a trialkylsilane. In all these cases, the reaction is suitable performed in the presence of a base. When using a halogenated hydrocarbon or alkoxy-substituted halogenated hydrocarbon as the protecting agent, the base is suitably an alkali metal hydride such as sodium hydride, potassium hydride or lithium hydride, an alkali metal amide such as sodium amide or potassium amide, an alkali metal alkoxide such as sodium methoxide or potassium ethoxide, or a metal salt of a dialkylsulphoxide such as sodium or potassium dimethylsulphoxide.

When using a trialkylsilane as the protecting agent, the base is suitably a tertiary amine such as trimethylamine, triethylamine or pyridine. The reaction can be carried out in the absence of any separate solvent, but it is preferred to use a solvent since the reaction then proceeds more smoothly. There are no particular limits on the choice of solvent, so long as it is inert to the reaction, and it may suitably be an ether such as tetrahydrofuran, dioxane or diethyl ether, a hydrocarbon such as benzene, toluene or cyclohexane, a dialkylformamide such as dimethylformamide, or a dialkylsulphoxide such as dimethylsulphoxide.

If the hydroxyl-protecting group is to be a carbonic ester residue such as ethoxycarbonyl, the protecting agent used is a corresponding halide such as ethoxycarbonyl chloride. This reaction is carried out in the presence of a base, for example an alkali or alkaline earth metal carbonate or bicarbonate such as sodium carbonate, potassium carbonate, calcium carbonate, sodium bicarbonate, potassium bicarbonate or calcium bicarbonate, a tertiary amine such as triethylamine, pyridine or N-methylpiperazine, an alkali or alkaline earth metal alkoxide such as sodium methoxide, potassium methoxide or calcium ethoxide, an alkali or alkaline earth metal hydride such as sodium hydride, potassium hydride or calcium hydride, or an alkali metal such as metallic sodium. It is preferred to use an organic base. The reaction can be carried out in the absence of any separate solvent, but the presence of a solvent is preferred because the reaction then proceeds more smoothly. Examples of suitable solvents are hydrocarbons such as benzene and toluene, and ethers such as diethyl ether, tetrahydrofuran and dioxane. However, if an excess of an organic base is used in the reaction, no other solvent is necessary.

If the hydroxyl-protecting group is to be an acyl group such as acetyl, the protecting agent used to treat the compound (IX) is an organic acid or reactive derivative thereof, such as acetic acid, acetic anhydride or acetyl chloride. The reaction is optionally performed in the presence of a solvent, for instance an amine such as pyridine or triethylamine, a halogenated hydrocarbon such as chloroform or dichloromethane, an ether such as diethyl ether, tetrahydrofuran or dioxane, a hydrocarbon such as benzene or toluene, or an ester such as ethyl acetate. The reaction temperature is not particularly critical, but it is generally preferred to carry out the reaction at a temperature of from 0°C to room temperature.

In the fifth step of the reaction scheme, the compound of formula (X) is subjected to catalytic reduction, so as to remove the benzyl group and give the compound of formula (XI). Any of the conventional reduction catalysts may be employed for this, for instance a platinum catalyst such as platinum oxide or colloidal platinum, a palladium catalyst such as palladium on carbon or palladium oxide, a nickel catalyst such as nickel oxide, Raney nickel or Urushibara nickel, or a cobalt catalyst such as Raney cobalt or Urushibara cobalt. The reduction is performed in a solvent: there are no particular limits on the choice of solvent, so long as it is inert to the reaction, but it is preferably water, an alcohol such as methanol, ethanol or ethylene glycol, an ether such as diethyl ether, dioxane or tetrahydrofuran, a hydrocarbon such as benzene, toluene, cyclohexane or methylcyclohexane, an ester such as ethyl acetate, or a carboxylic acid such as acetic acid. The reaction can be performed at atmospheric or superatmospheric pressure. The reaction temperature is not particularly critical, but it is generally preferred to perform it at around room temperature.

In the sixth step of the reaction scheme, the compound of formula (XI) is oxidized to the compound of formula (XII). The oxidizing agents and reaction conditions described hereinbefore for the oxidation of the compound of formula (II) can be used for this step, also.

In the seventh step, the compound (XIII) is prepared by reacting the compound (XII) with a Wittig reagent of formula

(XVII)

wherein $R^1$ has the meaning previously given, and $R^9$ represents a hydrocarbon group such as an aryl group (e.g. phenyl) or an alkyl group (e.g. n-butyl). The reaction conditions described hereinbefore with reference to the second step can be used for this step also.

In the eighth step, the carbonyl group of compound (XIII) is reduced, giving the compound of formula (XIV). Any reducing agent may be employed which is capable of converting a carbonyl group into a hydroxyl group without concomitantly reducing an ethylenic double bond, and it is preferably a metal hydride such as sodium borohydride, potassium borohydride, lithium borohydride, zinc borohydride, lithium tri-t-butoxyaluminium hydride, lithium trimethoxyaluminium hydride, sodium cyanoborohydride or lithium 9b-boraperhydrophenanthrene hydride. The reaction can be performed in the absence of any separate solvent, but the use of a solvent is preferred since the reaction then proceeds more smoothly. There are no particular limits on the choice of solvent, so long as it is inert to the reaction, but preferred examples are alcohols such as methanol, ethanol and isopropanol, and ethers such as tetrahydrofuran and dioxane. The reaction temperature is not particularly critical, but relatively low temperatures are preferred, so as to suppress side-reactions, it being generally preferable to operate at temperatures between −10°C and room temperature.

In the ninth step, the compound of formula (XV) is prepared by protecting the hydroxyl group of the compound of formula (XIV). There are no particular limits on the choice of protecting group to be used, provided that it is one which will not be removed during the subsequent removal of the protecting group $R^7$. The hydroxyl-protecting agents and reaction conditions described hereinbefore with reference to the fourth step can be used for this step, also.

In the tenth step of the reaction scheme, the compound of formula (II) is obtained by removing the hydroxyl-protecting group $R^7$ and, if appropriate, also the carboxyl-protecting group $R^6$. Depending upon the nature of the two protecting groups, the carboxyl-protecting group $R^6$ can sometimes be removed along with the hydroxyl-protecting group $R^7$, so that it may not be necessary to carry out a separate operation for removing $R^6$. If the carboxyl-protecting group $R^6$ is removed at this stage, the resulting carboxyl group can be left free, since it does not participate in the subsequent reactions for preparing the compound of formula (I). However, if the product of the tenth step is a mixture of isomers, separation of these isomers will be facilitated if the carboxyl group is protected. For this reason, if the protecting group $R^6$ is removed along with $R^7$ during the tenth step and a mixture of isomers is obtained, then it is generally preferred to reprotect the free carboxyl group.

The conditions for removing the hydroxyl-protecting group $R^7$ will depend on its nature, and are the same as described hereinbefore for the removal of the protecting group $R^3$ from compounds of formula (III). Similarly, if a separate operation has to be performed to remove the carboxyl-protecting group $R^6$, the conditions needed will depend on the nature of this protecting group and are the same as those described hereinbefore for the removal of the carboxyl-protecting group $R^2$ from compounds of formula (III). If the carboxyl-protecting group $R^6$ is removed and it is desired to reprotect the resulting free carboxyl group, this can be done by using the same protecting agents and reaction conditions as described hereinbefore with reference to the second step of the reaction scheme.

At the end of any of the reaction steps in the preparation of the compounds of formula (II), the desired product can be isolated from the reaction mixture by conventional techniques and, if necessary, purified by normal means, such as column chromatography or thin-layer chromatography. When mixtures of optical or geometrical isomers are obtained, they can be resolved by conventional techniques at a convenient point in the synthesis.

The invention is illustrated by the following Examples 1 to 8, while the subsequent Preparations 1 to 26 illustrate the synthesis of the starting materials of formula (II) and intermediates therefor.

EXAMPLE 1

9-Oxo-15α-hydroxy-5(6),10(11)α-bis-methyleneprost-13-trans-enoic acid and 9-oxo-15α-hydroxy-5(6),10(11)α-bis-methyleneisoprost-13-trans-enoic acid (1)
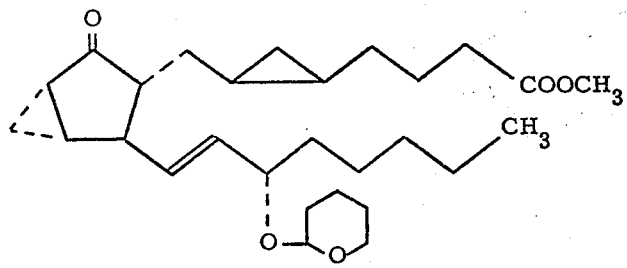

mixture was stirred for 30 minutes. After completion of the reaction, 50 ml of ether were added and the reaction mixture was filtered through "Celite" filter-aid. The filtrate was washed successively with 0.5N aqueous sodium hydroxide, water and 3% aqueous sodium bicarbonate, and dried over anhydrous sodium sulphate. The solvent was distilled off, giving 239 mg of crude methyl 9-oxo-15α-(2-tetrahydropyranyl)oxy-5(6),10(11)α-bis-methyleneprost-13-trans-enoate as an oil. IR spectrum (liquid film): $\nu_{max} = 1735$ cm$^{-1}$.

NMR spectrum (CDCl$_3$): δ = −0.5 to −0.2 and 0.5 to 0.8 (three-membered ring),
3.6 (3H, singlet, —COOC$\underline{H}_3$).

3.2–4.2 (3H, multiplet, 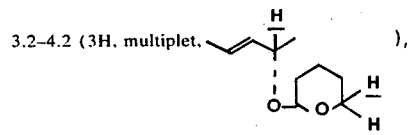 ), 4.7 (1H, multiplet, 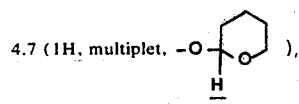 ), 5.0–6.0 (2H, multiplet, 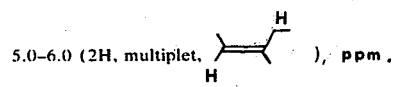 ), ppm.

(2)
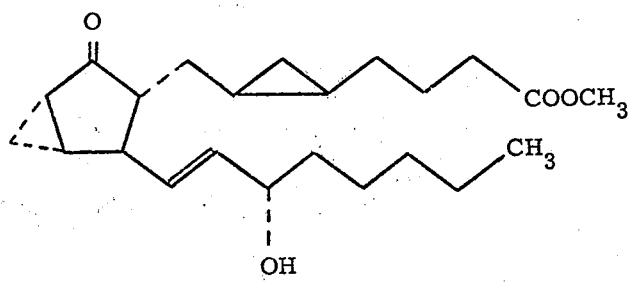

239 mg of methyl 9-oxo-15α-(2-tetrahydropyranyl)oxy-5(6),10(11)α-bis-methyleneprost-13-trans-enoate were dissolved in 10 ml of a mixture of acetic acid, water and tetrahydrofuran (20:10:3), and the solution was stirred at 40°C for 1.5 hours. After completion of dichloromethane, 700 mg of chromic anhydride/pyridine complex (Collins reagent) were added, and the 245 mg of methyl 9α-hydroxy-15α-(2-tetrahydropyranyl)oxy-5(6),10(11)α-bis-methyleneprost-13-trans-enoate were dissolved in 25 ml of anhydrous the reaction. 20 ml of ethyl acetate, 10 ml of water and 10 ml of a saturated aqueous sodium chloride solution were added to the reaction mixture, and the resulting layers were separated. The aqueous layer was further extracted with two 10 ml portions of ethyl acetate. The organic layers thus obtained were combined and dried over anhydrous sodium sulphate. The solvent was distilled off, and the residue thus obtained was purified by silica gel column chromatography, to yield 165 mg of methyl 9-oxo-15α-hydroxy-5(6),10(11)α-bis-methyleneprost-13-trans-enoate as an oil. IR spectrum (liquid film): $\nu_{max} = 3450, 1730$ cm$^{-1}$.

NMR spectrum (CDCl$_3$): δ = −0.5 to −0.2 and 0.5 to 0.8 (three-membered ring),
3.6 (3H, singlet, —COOC$\underline{H}_3$), 3.9–4.2 (1H, multiplet, ), 5.1–6.0 (2H, multiplet, ), ppm.

Mass spectrum: 376 (M$^+$), 358 (M$^+$ − 18).

165 mg of methyl 9-oxo-15α-hydroxy-5(6),10(11)α-bis-methyleneprost-13-trans-enoate were dissolved in 3 ml of tetrahydrofuran, 2 ml of 1N aqueous sodium hydroxide solution and 1 ml of methanol were added to the solution, and the resulting mixture was stirred at room temperature for 2 hours. After completion of the reaction, the reaction mixture was acidified by addition of 1.5 ml of a saturated aqueous oxalic acid solution, and extracted with one 25 ml portion and two 10 ml portions of ethyl acetate. The combined extracts were washed with 10 ml of saturated aqueous sodium chloride solution and dried over anhydrous sodium sulphate. The solvent was distilled off from the extract, and the residue was purified by column chromatography on silica gel washed with acid, to yield 115 mg of a mixture of 9-oxo-15α-hydroxy-5(6),10(11)α-bis-methyleneprost-13-trans-enoic acid and 9-oxo-15α-hydroxy-5(6),10(11)α-bis-methyleneisoprost-13-trans-enoic acid as an oil. IR spectrum (liquid film): $\nu_{max} = 3400, 1720 - 1700$ cm$^{-1}$.

NMR spectrum (CDCl$_3$): δ = −0.5 to −0.2 and 0.5 to 0.8 (three-membered ring), 3.9–4.2 (1H, multiplet, ), 5.4–5.8 (2H, multiplet, ), 6.7 (2H, broad, singlet, —O$\underline{H}$ and —COO$\underline{H}$), ppm.

Mass spectrum: 362 (M$^+$), 344 (M$^+$ −18), 291 (M$^+$ −71), 273 (M$^+$ −89).

(3)

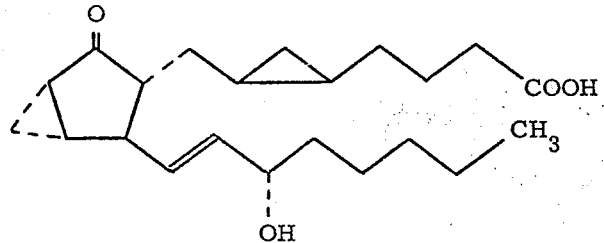

and

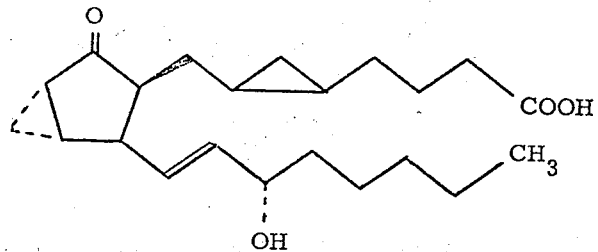

(4)

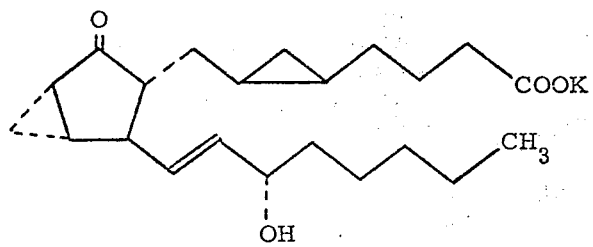

163 mg of 9-oxo-15α-hydroxy-5(6),10(11)α-bis-methyleneprost-13-trans-enoic acid were dissolved in 5 ml of 50% aqueous methanol, 31 mg of potassium carbonate were added, and the mixture was stirred at room temperature for 1 hour. After completion of the reaction, the solvent was distilled off under reduced pressure from the reaction mixture, to leave 178 mg of potassium 9-oxo-15α-hydroxy-5(6),10(11)α-bis-methyleneprost-13-trans-enoate as a white wax. IR spectrum ("Nujol" – Trade Mark): $\nu_{max}$ = 1715, 1585, 1407 cm$^{-1}$.

EXAMPLE 2

9-Oxo-15β-hydroxy-5(6),10(11)α-bis-methyleneprost-13-trans-enoic acid and 9-oxo-15β-hydroxy-5(6),10(11)α-bis-methyleneisoprost-13-trans-enoic acid 427 mg of methyl 9α-hydroxy-15β-(2-tetrahydropyranyl)oxy-5(6),10(11)α-bis-methyleneprost-13-trans-enoate were dissolved in 40 ml of anhydrous dichloromethane, 2.0 g of chromic anhydride/pyridine complex (Collins reagent) were added to the solution under ice-cooling, and the mixture was stirred for 30 minutes. After completion of the reaction, the reaction mixture was treated in the same manner as in Example 1 - (1), to give 408 mg of crude methyl 9-oxo-15β-(2-tetrahydropyranyl)oxy-5(6),10(11)α-bis-methyleneprost-13-trans-enoate as an oil.

The IR spectrum and NMR spectrum of this product were identical with those of the methyl 9-oxo-15α-(2-tetrahydropyranyl)oxy-5(6),10(11)α-bis-methyleneprost-13-trans-enoate obtained in Example 1 - (1).

(2)

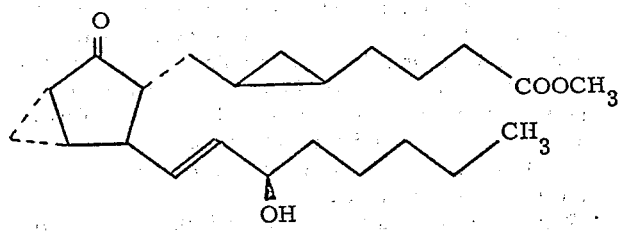

408 mg of methyl 9-oxo-15β-(2-tetrahydropyranyl)oxy-5(6),10(11)α-bis-methyleneprost-13-trans-enoate were dissolved in 10 ml of a mixture of acetic acid, water and tetrahydrofuran (20:10:3), and the solution was stirred at 40°C for 2.5 hours. After completion of the reaction, the reaction mixture was treated in the same manner as in Example 1 - (2), to give 228 mg of methyl 9-oxo-15β-hydroxy-5(6),10(11)α-bis-methyleneprost-13-trans-enoate as an oil.

The IR spectrum, NMR spectrum and Mass spectrum of this product were identical with those of the methyl 9-oxo-15α-hydroxy-5(6),10(11)α-bis-methyleneprost-13-trans-enoate obtained in Example 1 - (2).

(1)

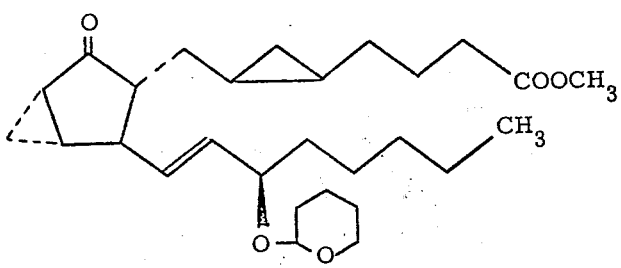

(3)

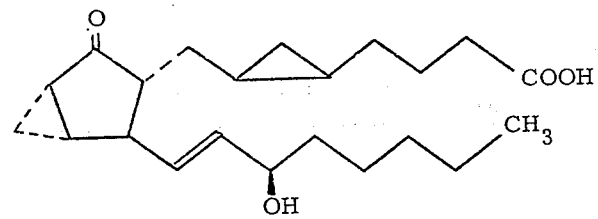

and

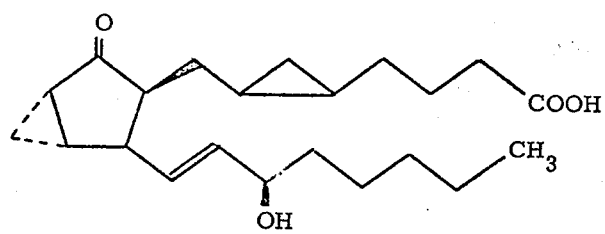

176 mg of methyl 9-oxo-15β-hydroxy-5(6),10(11)α-bis-methyleneprost-13-trans-enoate were dissolved in 3 ml of tetrahydrofuran, 2 ml of 1N aqueous sodium hydroxide solution and 1 ml of methanol were added to the solution, and the mixture was stirred at room temperature for 1.5 hours. After completion of the reaction, the reaction mixture was treated in the same manner as in Example 1 - (3), to give 33 mg of 9-oxo-15β-hydroxy-5(6),10(11)α-bis-methyleneprost-13-trans-enoic acid (having the greater polarity), 70 mg of 9-oxo-15β-hydroxy-5(6),10(11)α-bis-methyleneisoprost-13-trans-enoic acid (having the smaller polarity), and 27 mg of their mixture, all as oils.

9-Oxo-15β-hydroxy-5(6),10(11)α-bis-methyleneprost-13-trans-enoic acid:
IR spectrum (liquid film): $\nu_{max}$ = 3400, 1720 – 1700 cm$^{-1}$.

---

NMR spectrum (CDCl$_3$): δ = −0.5 to −0.2 and 0.4 to 0.8 (three-membered ring), 2.6–2.9 (1H, multiplet, 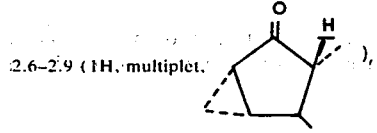 ), 3.9–4.3 (1H, multiplet, 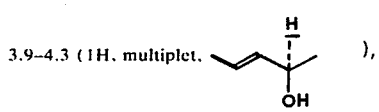 ), 5.3,5.8 (2H, multiplet, 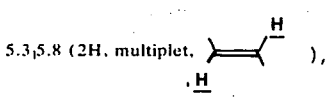 ), 5.9 (2H, broad, singlet, —O$\underline{H}$ and —COO$\underline{H}$), ppm.

---

Mass spectrum: 362 (M$^+$), 344 (M$^+$ −18), 291 (M$^+$ −71).

9-Oxo-15β-hydroxy-5(6),10(11)α-bis-methyleneisoprost-13-trans-enoic acid:
IR spectrum (liquid film): $\nu_{max}$ = 3400, 1720 – 1700 cm$^{-1}$.

---

NMR spectrum (CDCl$_3$): δ = −0.5 to −0.2 and 0.4 to 0.8 (three-membered ring), 2.8–3.1 (1H, multiplet, 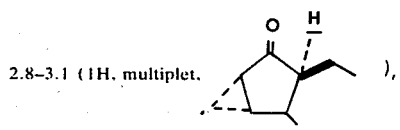 ), 3.9–4.3 (1H, multiplet, 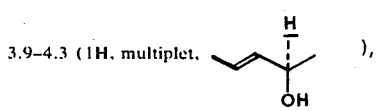 ), 5.4–5.6 (2H, multiplet, 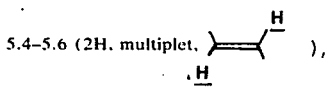 ), 6.1 (2H, broad, singlet, —O$\underline{H}$ and —COO$\underline{H}$), ppm.

---

Mass spectrum: 362 (M$^+$), 344 (M$^+$ −18), 291 (M$^+$ −71).

EXAMPLE 3

9-Oxo-15α-hydroxy-5(6),10(11)α-bis-methyleneprost-13-trans-enoic acid (1)

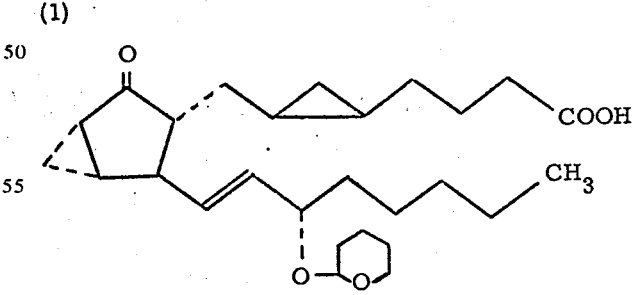

548 mg of 9α-hydroxy-15α-(2-tetrahydropyranyl)oxy-5(6), 10(11)α-bis-methyleneprost-13-trans-enoic acid were dissolved in 50 ml of anhydrous dichloromethane, 2.56 g of chromic anhydride/pyridine complex (Collins reagent) were added to the solution under ice-cooling, and the mixture was stirred at room temperature for 30 minutes. After completion of the reaction, ether was added and the reaction mixture was filtered through "Celite" filter-aid. The filtrate was washed successively with dilute hydrochloric acid and water, and dried over anhydrous sodium sulphate. The solvent was distilled off, leaving 425 mg of crude 9-oxo-15α-(2-tetrahydropyranyl)oxy-5(6),10(11)α-bis-methyleneprost-13-trans-enoic acid as a dark brown oil.

---

NMR spectrum (CDCl$_3$): δ = −0.5 to −0.2 and 0.5 to 0.8 (three-membered ring), 2.6–2.9 (1H, broad, 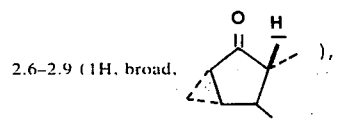 ), 3.2–4.2 (3H, broad, 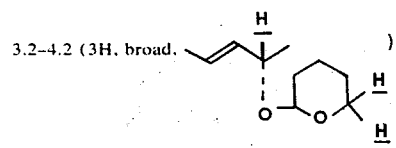 ), 4.9 (1H, broad, 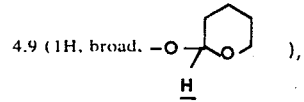 ), 5.7 (2H, broad, 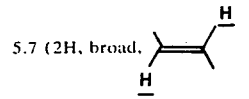 ), 7.2 (1H, broad, —COO$\underline{H}$), ppm.

---

420 mg of 9-oxo-15α-(2-tetrahydropyranyl)oxy-5(6),10(11)α-bis-methyleneprost-13-trans-enoic acid were dissolved in 30 ml of a mixture of acetic acid, water and tetrahydrofuran (20:10:3), and this solution was stirred at room temperature for 5 hours. After completion of the reaction, 100 ml of water were added and the reaction mixture was extracted with two 50 ml portions and three 30 ml portions of ether. The combined extracts were dried over anhydrous sodium sulphate and the solvent was distilled off. The 300 mg of residue thus obtained were purified by silica gel column chromatography, to yield 247 mg of 9-oxo-15α-hydroxy-5(6),10(11)α-bis-methyleneprost-13-trans-enoic acid as a pale yellow oil. IR spectrum (liquid film): ν$_{max}$ = 3400, 1710 cm$^{-1}$.

---

NMR spectrum (CDCl$_3$): δ = −0.5 to 0.1 and 0.6 to 0.8 (three-membered ring), 2.6–2.9 (1H, multiplet, 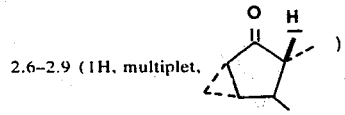 ), 4.0–4.4 (1H, multiplet, 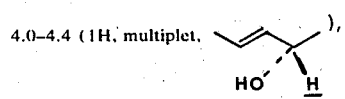 ), 5.4–6.1 (2H, multiplet, 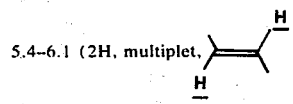 ), 6.8 (2H, broad, singlet, —O$\underline{H}$ and —COO$\underline{H}$), ppm.

---

EXAMPLE 4

9-Oxo-15β-hydroxy-5(6),10(11)α-bis-methyleneprost-13-trans-enoic acid (2)

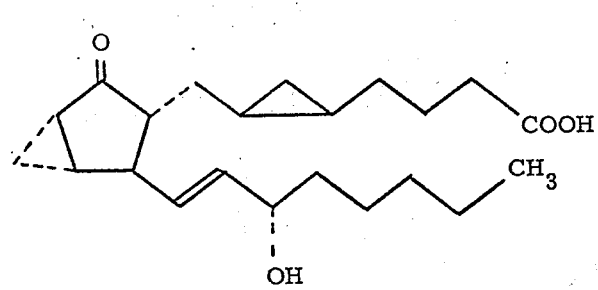

(1)

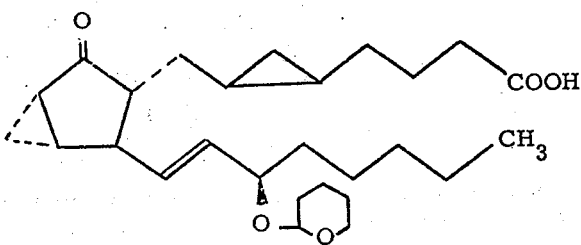

704 mg of 9α-hydroxy-15β-(2-tetrahydropyranyl)oxy-5(6),10(11)α-bis-methyleneprost-13-trans-enoic acid were dissolved in 70 ml of anhydrous dichloromethane, 3.4 g of chromic anhydride/pyridine complex (Collins reagent) were added to the solution under ice-cooling, and the mixture was stirred at room temperature for 30 minutes. After completion of the reaction, the reaction mixture was treated in the same manner as in Example 3 -(1), to give 563 mg of crude 9-oxo-15β-(2-tetrahydropyranyl)oxy-5(6),10(11)α-bis-methyleneprost-13-trans-enoic acid as an oil.

The NMR spectrum of this product was identical with that of the 9-oxo-15α-(2-tetrahydropyranyl)oxy-5(6),10(11)α-bis-methyleneprost-13-trans-enoic acid obtained in Example 3 - (1).

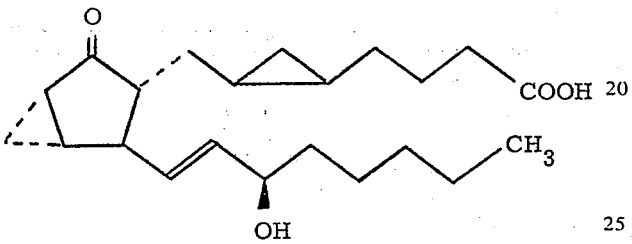

558 mg of 9-oxo-15β-(2-tetrahydropyranyl)oxy-5(6),10(11)α-bis-methyleneprost-13-trans-enoic acid were dissolved in 50 ml of a mixture of acetic acid, water and tetrahydrofuran (20:10:3), and the solution was stirred at room temperature for 8 hours. After completion of the reaction, the reaction mixture was treated in the same manner as in Example 3 -(2), to give 314 mg of 9-oxo-15β-hydroxy-5(6),10(11)α-bis-methyleneprost-13-trans-enoic acid as an oil.

The IR spectrum and NMR spectrum of this product were identical with those of the corresponding product obtained in Example 2.

EXAMPLE 5

9-Oxo-15α-hydroxy-20-ethyl-5(6),10(11)α-bis-methyleneprost-13-trans-enoic acid (1)

564 mg of 9-hydroxy-15α-(2-tetrahydropyranyl)oxy-20-ethyl-5(6),10(11)α-bis-methyleneprost-13-trans-enoic acid were dissolved in 50 ml of anhydrous dichloromethane, 1.80 g of chromic anhydride/pyridine complex (Collins reagent) were added to the solution under ice-cooling, and the mixture was stirred at room temperature for 30 minutes. After completion of the reaction, the reaction mixture was treated in the same manner as in Example 3 -(1), to give 505 mg of crude 9-oxo-15α-(2-tetrahydropyranyl)oxy-20-ethyl-5(6),10(11)α-bis-methyleneprost-13-trans-enoic acid as a dark brown oil.

NMR spectrum (CDCl₃: δ = −0.5 to −0.2 and 0.5 to 0.8 (three-membered ring), 2.6–2.9 (1H, broad, 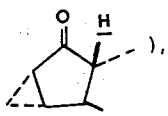 ), 3.2–4.3 (3H, broad, 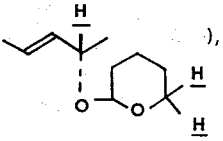 ), 4.9 (1H, broad, 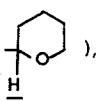 ), 5.7 (2H, broad,  ), 7.4 (1H, broad, —COOH), ppm.

(2)

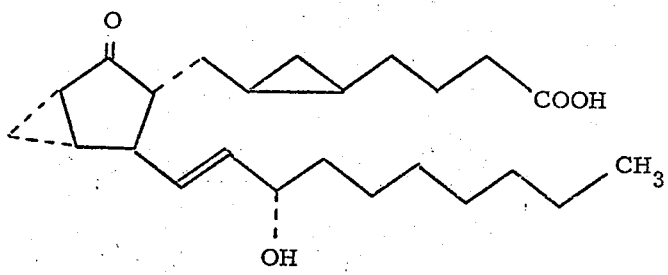

505 mg of 9-oxo-15α-(2-tetrahydropyranyl)oxy-20-ethyl-5(6),10(11)α-bis-methyleneprost-13-trans-enoic

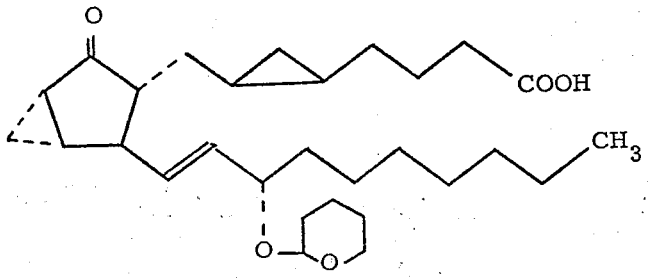

acid were dissolved in 30 ml of a mixture of acetic acid, water and tetrahydrofuran (20:10:3), and the solution was stirred at room temperature for 5 hours. After completion of the reaction, the reaction mixture was treated in the same manner as in Example 3 - (2), to give 259 mg of 9-oxo-15α-hydroxy-20-ethyl-5(6),10(11)α-bis-methyleneprost-13-trans-enoic acid as a pale yellow oil. IR spectrum (liquid film): $\nu_{max}$ = 3380, 1710 cm$^{-1}$.

---

NMR spectrum (CDCl$_3$): δ = −0.5 to −0.1 and 0.5 to 0.8 (three-membered ring), 2.6–2.9 (1H, multiplet, 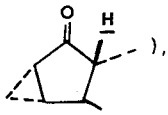 ), 4.1–4.4 (1H, multiplet,  ), 5.4–6.1 (2H, multiplet, 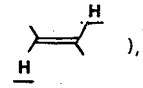 ), 7.2 (2H, broad, singlet, —O$\underline{H}$ and —COO$\underline{H}$), ppm.

EXAMPLE 6

9-Oxo-15β-hydroxy-20-ethyl-5(6),10(11)α-bis-methyleneprost-13-trans-enoic acid (1)

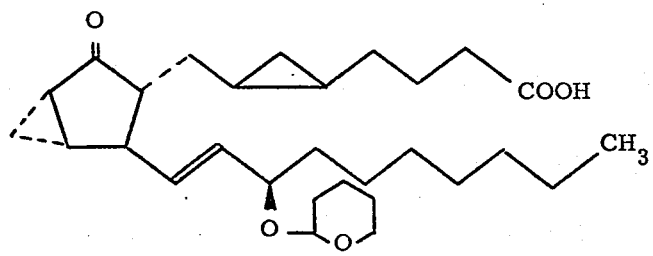

672 mg of 9α-hydroxy-15β-(2-tetrahydropyranyl-)oxy-20-ethyl-5(6),10(11)α-bis-methyleneprost-13-trans-enoic acid were dissolved in 70 ml of anhydrous dichloromethane, 2.2 g of chromic anhydride/pyridine complex (Collins reagent) were added to the solution under ice-cooling, and the mixture was stirred at room temperature for 40 minutes. After completion of the reaction, the reaction mixture was treated in the same manner as in Example 3 - (1), to give 611 mg of crude 9-oxo-15β-(2-tetrahydropyranyl)oxy-20-ethyl-5(6),10(11)α-bis-methyleneprost-13-trans-enoic acid as an oil.

The NMR spectrum of this product was identical with that of the 9-oxo-15α-(2-tetrahydropyranyl)oxy-20-ethyl-5(6),10(11)α-bis-methyleneprost-13-trans-enoic acid obtained in Example 5 -(1).

(2)

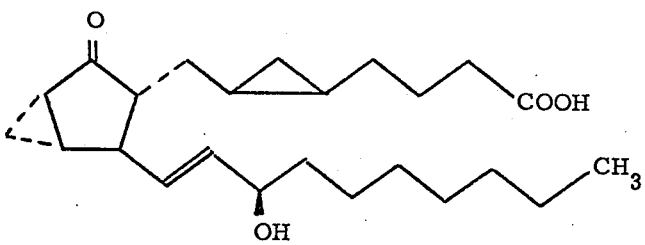

611 mg of 9-oxo-15β-(2-tetrahydropyranyl)oxy-20-ethyl-5(6),10(11)α-bis-methyleneprost-13-trans-enoic acid were dissolved in 30 ml of a mixture of acetic acid, water and tetrahydrofuran (20:10:3), and the solution was stirred at room temperature for 7 hours. After completion of the reaction, the reaction mixture was treated in the same manner as in Example 3 - (2), to give 252 mg of 9-oxo-15β-hydroxy-20-ethyl-5(6),10(11)α-bis-methyleneprost-13-trans-enoic acid as an oil.

The IR spectrum and NMR spectrum of this product were identical with those of the 9-oxo-15α-hydroxy-20-ethyl-5(6),10(11)α-bis-methyleneprost-13-trans-enoic acid obtained in Example 5.

EXAMPLE 7

9-Oxo-15α-hydroxy-20-n-butyl-5(6),10(11)α-bis-methyleneprost-13-trans-enoic acid (1)

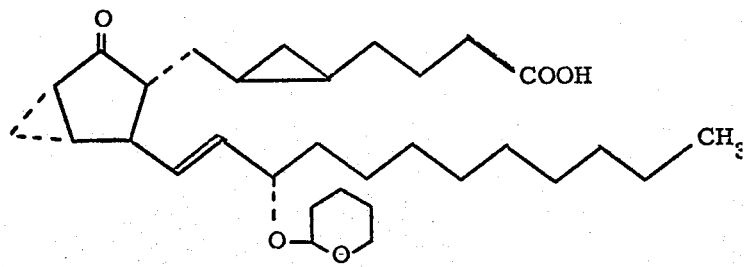

996 mg of 9α-hydroxy-15α-(2-tetrahydropyranyl-)oxy-20-n-butyl-5(6),10(11)α-bis-methyleneprost-13-trans-enoic acid were dissolved in 100 ml of anhydrous dichloromethane, 3.0 g of chromic anhydride/pyridine complex (Collins reagent) were added to the solution under ice-cooling, and the mixture was stirred at room temperature for 30 minutes. After completion of the reaction, the reaction mixture was treated in the same manner as in Example 3 - (1), to give 710 mg of crude 9-oxo-15α-(2-tetrahydropyranyl)oxy-20-n-butyl-5-(6),10(11)α-bis-methyleneprost-13-trans-enoic acid as a dark brown oil.

NMR spectrum (CDCl₃): δ = −0.5 to −0.2 and 0.5 to 0.8 (three-membered ring), 2.6–2.9 (1H, broad, 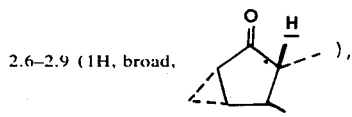 ), 3.2–4.2 (3H, broad,  ), 4.9 (1H, broad, -O<image>), 5.7 (2H, broad, <image> ), 7.1 (1H, broad, —COOH), ppm.

688 mg of 9-oxo-15α-(2-tetrahydropyranyl)oxy-20-n-butyl-5(6),10(11)α-bis-methyleneprost-13-trans-enoic acid were dissolved in 50 ml of a mixture of acetic acid, water and tetrahydrofuran (20:10:3), and the solution was stirred at room temperature for 7 hours. After completion of the reaction, the reaction mixture was treated in the same manner as in Example 3 - (2), to give 392 mg of 9-oxo-15α-hydroxy-20-n-butyl-5(6),10(11)α-bis-methyleneprost-13-trans-enoic acid as a pale yellow oil. IR spectrum (liquid film): $\nu_{max}$ = 3400, 1710 cm⁻¹.

NMR spectrum (CDCl₃): δ = −0.5 to −0.2 ad 0.5 to 0.8 (three-membered ring), 2.6–2.9 (1H, multiplet, 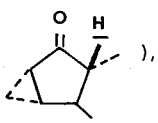 ), 4.1–4.4 (1H, multiplet, 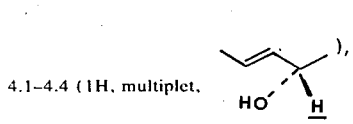 ), 5.4–6.1 (2H, multiplet, 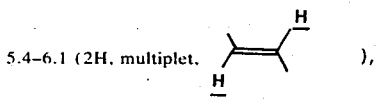 ), 6.4 (2H, broad, singlet, —OH and —COOH), ppm.

EXAMPLE 8

9-Oxo-15β-hydroxy-20-n-butyl-5(6),10(11)α-bis-methyleneprost-13-trans-enoic acid (2)

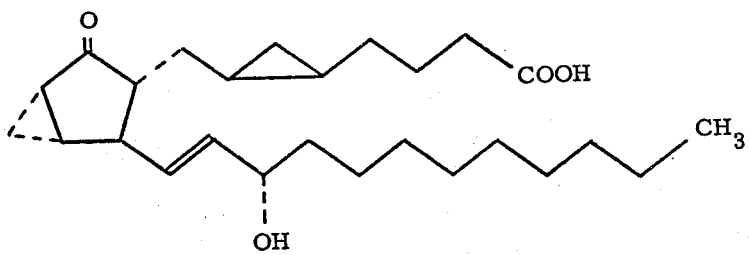

(1)

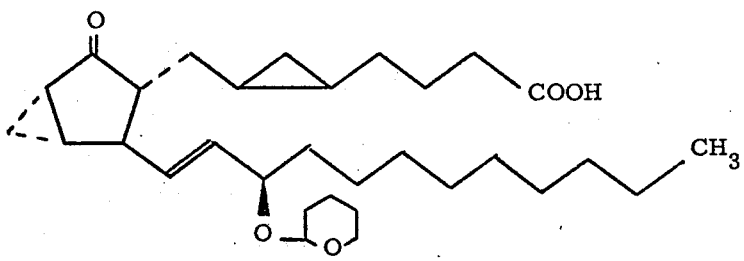

997 mg of 9α-hydroxy-15β-(2-tetrahydropyranyl)oxy-20-n-butyl-5(6),10(11)α-bis-methyleneprost-13-trans-enoic acid were dissolved in 100 ml of anhydrous dichloromethane, 3.0 g of chromic anhydride/pyridine complex (Collins reagent) were added to the solution under ice-cooling, and the mixture was stirred at room temperature for 30 minutes. After completion of the reaction, the reaction mixture was treated in the same manner as in Example 3 - (1), to give 648 mg of crude 9-oxo-15β-(2-tetrahydropyranyl)oxy-20-n-butyl-5(6),10(11)α-bis-methyleneprost-13-trans-enoic acid as an oil.

The NMR spectrum of this product was identical with that of the 9-oxo-15α-(2-tetrahydropyranyl)oxy-20-n-butyl-5(6),10(11)α-bis-methyleneprost-13-trans-enoic acid obtained in Example 7 - (1).

hour. After completion of the reaction, 30 ml of methanol were added to the reaction mixture. The temperature of the mixture was raised to room temperature, and 100 ml of saturated aqueous potassium sodium tartarate solution was added to decompose the excess aluminium compound. The aqueous and organic layers of the reaction mixture were separated, the organic layer was reserved, and the aqueous layer was extracted with three 50 ml portions of ethyl acetate. The ethyl acetate extracts and the reserved organic layer were combined, washed with 100 ml of saturated aqueous sodium chloride solution, and dried over anhydrous sodium sulphate. The solvent was distilled off, leaving an oil which was purified by silica gel column chromatography. The purified oil crystallized on ice-cooling to yield 21.54 g of the desired compound. IR spectrum (2)

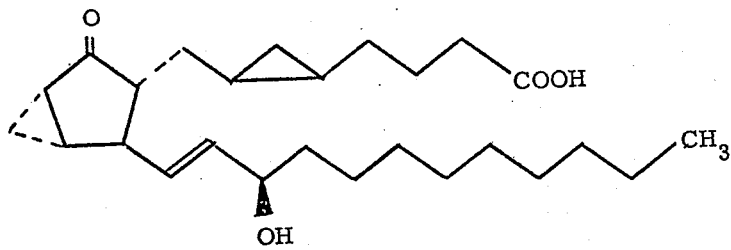

648 mg of 9-oxo-15β-(2-tetrahydropyranyl)oxy-20-n-butyl-5(6),10(11)α-bis-methyleneprost-13-trans-enoic acid were dissolved in 50 ml of a mixture of acetic acid, water and tetrahydrofuran (20:10:3), and the mixture was stirred at room temperature for 11 hours. After completion of the reaction, the reaction mixture was treated in the same manner as in Example 3 - (2), to give 436 mg of 9-oxo-15β-hydroxy-20-n-butyl-5(6),10(11)α-bis-methyleneprost-13-trans-enoic acid as an oil.

The IR spectrum and NMR spectrum of this product were identical with those of the 9-oxo-15α-hydroxy-20-n-butyl-5(6),10(11)α-bis-methyleneprost-13-trans-enoic acid obtained in Example 7.

Preparation 1

2α-Hydroxy-5β-benzyloxymethylcyclopent-3-en-1α-yl-acetaldehyde γ-lactol

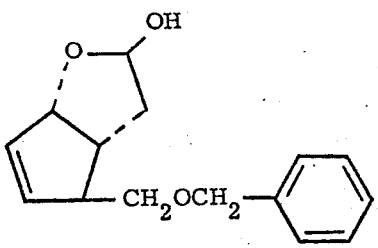

24.2 g of 2α-hydroxy-5β-benzyloxymethylcyclopent-3-en-1α-yl-acetic acid γ-lactone were dissolved in 700 ml of anhydrous toluene, under a stream of argon, 170 ml of a toluene solution of 25% di-isobutylaluminium hydride were added dropwise at −60°C, and the resulting mixture was stirred at the same temperature for one (liquid film): $\nu_{max}$= 3400 cm$^{-1}$.

NMR spectrum (CDCl$_3$): δ = 3.4 (2H, doublet, —C$\underline{H}_2$O—),

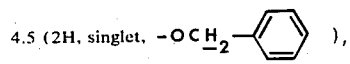

5.0–5.6 (2H, multiplet, 

and 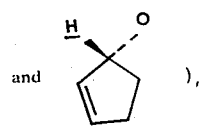 ), 5.6–5.9 (2H, multiplet, 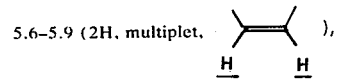 ), 7.3 (5H, singlet, hydrogens of benzene ring), ppm.

Mass spectrum: 246 (M$^+$).

Preparation 2

Methyl 7-[2α-hydroxy-5β-benzyloxymethylcyclopent-3-en-1α-yl]-hept-5-cis-enoate

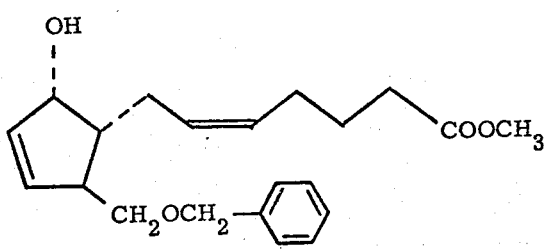

39.1 g of sodium hydride (purity 53%) and 860 ml of dimethylsulphoxide were stirred at a temperature below 75°C for 1 hour, then a solution of 148.3 g of 5-triphenylphosphoniopentanoic acid bromide in 800 ml of dimethylsulphoxide was added at room temperature, followed by a solution of 21.0 g of 2α-hydroxy-5β-benzyloxymethylcyclopent-3-en-1α-yl-acetaldehydeγ-lactol in 150 ml of dimethylsulphoxide. The resulting mixture was stirred at room temperature for 53 hours.

After completion of the reaction, the reaction mixture was added with stirring to 2 liters of ice-water. This mixture was acidified to pH 2.8 with oxalic acid, and extracted successively with one 2 liter portion and three 400 ml portions of ethyl acetate. The combined extracts were washed with two 300 ml portions of saturated aqueous sodium chloride solution and dried over anhydrous sodium sulphate. The solvent was distilled off from the extract, leaving a residue which was dissolved in ether. Diazomethane was added under ice-cooling to the ether solution until the yellow diazomethane colour no longer disappeared. After completion of the reaction, the solvent was distilled off from the reaction mixture, leaving an oil which was purified by silica gel column chromatography to give 13.7 g of the desired compound as a pale yellow oil. IR spectrum (liquid film): $\nu_{max}$= 3450, 1735 cm$^{-1}$.

NMR spectrum (CDCl$_3$): δ = 3.2–3.6 (2H, multiplet, —C$\underline{H}_2$O—), 3.6 (3H, singlet, —COOC$\underline{H}_3$),

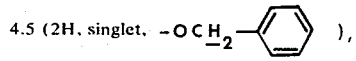
4.5 (2H, singlet, —OC$\underline{H}_2$—⌬ ),

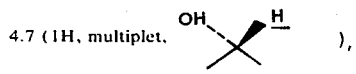
4.7 (1H, multiplet, ),

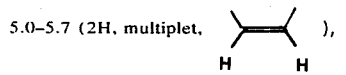
5.0–5.7 (2H, multiplet, ),

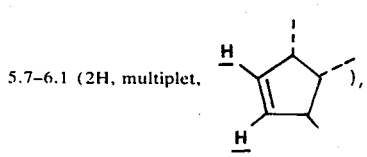
5.7–6.1 (2H, multiplet, ), 7.3 (5H, singlet, hydrogens of benzene ring), ppm.

Mass spectrum: 344 (M$^+$).
Preparation 3

Methyl 7-[2α-hydroxy-5β-benzyloxymethyl-3(4)α-methylenecyclopent-1α-yl]-5(6)-methyleneheptanoate

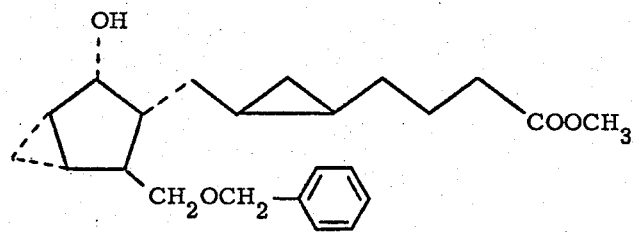

3.95 g of methyl 7-[2α-hydroxy-5β-benzyloxymethylcyclopent-3-en-1α-yl]hept-5-enoate were dissolved in 515 ml of anhydrous isopropyl ether, 51.3 ml of an n-hexane solution of 25% diethyl zinc and 8.4 ml of methylene iodide were added with ice-cooling and under a stream of argon, and the resulting mixture was stirred at room temperature for 4 hours. After completion of the reaction, 250 ml of diethyl ether and 150 ml of saturated aqueous potassium sodium tartarate solution were added, with cooling to decompose any unreacted zinc complex. The aqueous and organic layers were separated, the organic layer was reserved, and the aqueous layer was extracted with three 60 ml portions of ether. The ether extracts and the reserved organic layer were combined and dried over anhydrous sodium sulphate. The solvent was distilled off, leaving an oil which was purified by silica gel column chromatography to give 3.10 g of the desired compound as an oil. IR spectrum (liquid film): $\nu_{max}$= 3470, 1738 cm$^{-1}$.

NMR spectrum (CDCl$_3$): δ = −0.4 to −0.1 ad 0.4 to 0.8 (three-membered ring),
3.6 (3H, singlet, —COOC$\underline{H}_3$),

4.5 (2H, singlet, —OC$\underline{H}_2$—⌬ ),

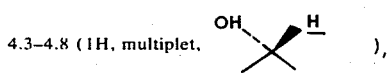
4.3–4.8 (1H, multiplet, ), 7.3 (5H, singlet, hydrogens of benzene ring), ppm.

Mass spectrum: 372 (M$^+$)
Preparation 4

Methyl 7-[2α-acetoxy-5β-benzyloxymethyl-3(4)α-methylenecyclopent-1α-yl]-5(6)-methyleneheptanoate

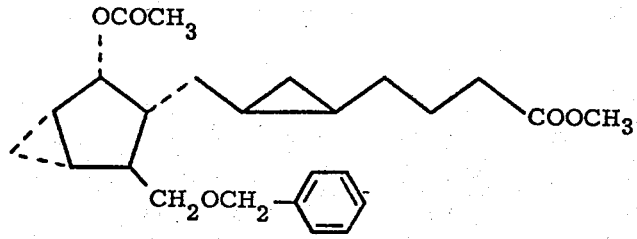

3.10 g of methyl 7-[2α-hydroxy-5β-benzyloxymethyl-3(4)α-methylenecyclopent-1α-yl]-5(6)- methyleneheptanoate were dissolved in 20 ml of anhydrous dichloromethane, 26 ml of pyridine and 20 ml of acetic anhydride were added to the solution under ice-cooling, and the mixture was stirred overnight at room temperature. After completion of the reaction, 40 ml of water were added and the reaction mixture was extracted with one 40 ml portion and three 20 ml portions of ether. The ether extracts were combined and dried over anhydrous sodium sulphate. The solvent was distilled off, leaving a residue which was purified by silica gel column chromatography to yield 3.32 g of the desired compound as an oil. IR spectrum (liquid film): $\nu_{max}$= 1735 cm$^{-1}$.

NMR spectrum (CDCl$_3$): δ = −0.5 to −0.2 and 0.4 to 0.8 (three-membered ring), 3.4 (2H, doublet, -C$\underline{H}_2$OCH$_2$- 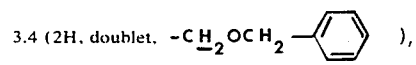 ), 3.6 (3H, singlet, —COOC$\underline{H}_3$), 4.5 (2H, singlet, -OC$\underline{H}_2$- 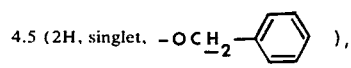 ), 5.3–5.6 (1H, doublet of doublets, 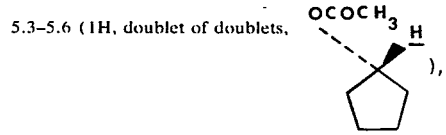 ), 7.3 (5H, singlet, hydrogens of benzene ring), ppm.

Mass spectrum: 414 (M$^+$), 354 (M$^+$ - 60).

Preparation 5

Methyl 7-[2α-acetoxy-5β-hydroxymethyl-3(4)α-methylenecyclopent-1α-yl]-5(6)-methyleneheptanoate

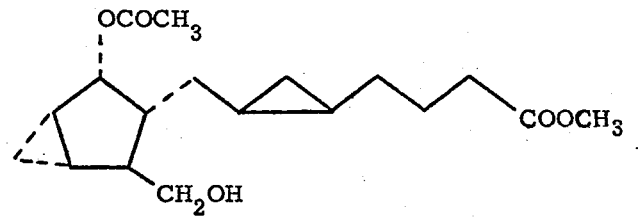

2.10 g of methyl 7-[2α-acetoxy-5β-benzyloxymethyl-3(4)α-methylenecyclopent-1α-yl]-5(6)-methyleneheptanoate were dissolved in 60 ml of methanol, 1.4 g of 10% palladium on carbon catalyst were added, and hydrogen was introduced into the mixture. Absorption of hydrogen completely ended in about 4 hours. After completion of the reaction, the catalyst was filtered off from the reaction mixture, and the solvent was distilled off. The residue thus obtained was purified by silica gel column chromatography to yield 1.63 g of the desired compound as an oil.

IR spectrum (liquid film): $\nu_{max}$= 3420, 1730 cm$^{-1}$.

NMR spectrum (CDCl$_3$): δ = −0.5 to −0.2 and 0.4 to 0.8 (three-membered ring),
2.1 (3H, singlet, —OCOC$\underline{H}_3$),
3.7 (3H, singlet, —COOC$\underline{H}_3$),
3.5–3.8 (2H, multiplet, —C$\underline{H}_2$OH), 5.5 (1H, doublet of doublets, 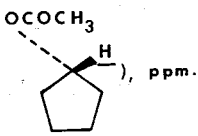 ), ppm.

Mass spectrum: 324 (M$^+$).

Preparation 6

Methyl 7-[2α-acetoxy-5β-formyl-3(4)α-methylenecyclopent-1α-yl]-5(6)-methyleneheptanoate

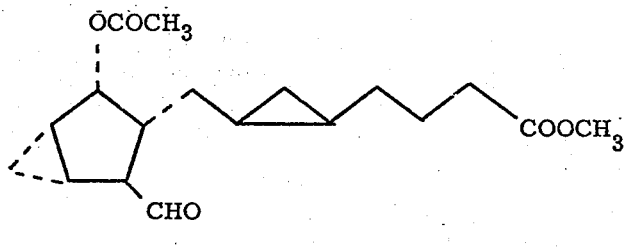

1.63 g of methyl 7-[2α-acetoxy-5β-hydroxymethyl-3(4)α-methylenecyclopent-1α-yl]-5(6)-methyleneheptanoate were dissolved in 75 ml of anhydrous dichloromethane, 4.5 g of chromic anhydride/pyridine complex (Collins reagent) were added under ice-cooling, and the mixture was stirred for 30 minutes. After completion of the reaction, 150 ml of ether were added and the reaction mixture was filtered through "Celite" filter-aid. The filtrate was washed with two 30 ml portions of 2% aqueous sodium hydroxide solution, then successively with water, 1N hydrochloric acid, water, 3% aqueous sodium bicarbonate solution and again water, and dried over anhydrous sodium sulphate. The solvent was distilled off, leaving the crude desired compound as an oil, which was used as such in Preparation 7.
IR spectrum (liquid film): $\nu_{max}=$ 1735 cm$^{-1}$.

NMR spectrum (CDCl$_3$): δ = −0.5 to −0.1 and 0.5 to 0.8 (three-membered ring),
2.1 (3H, singlet, —OCOC$\underline{H}_3$),
3.7 (3H, singlet, —COOC$\underline{H}_3$), 5.3–5.7 (1H, quartet, 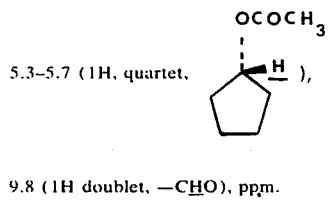 ), 9.8 (1H doublet, —C$\underline{H}$O), ppm.

Preparation 7

Methyl 9α-acetoxy-15-oxo-5(6),10(11)α-bis-methyleneprost-13-transenoate

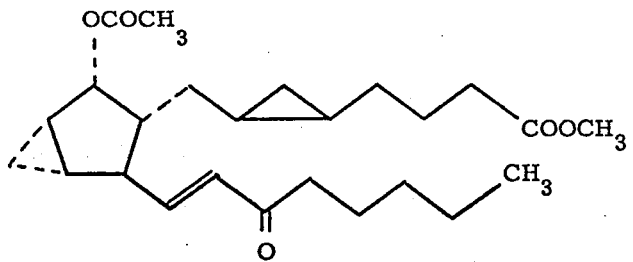

The methyl 7-[2α-acetoxy-5β-formyl-3(4)α-methylenecyclopent-1α-yl]-5(6)-methyleneheptanoate obtained in Preparation 6 was dissolved in 30 ml of anhydrous ether, 1.88 g of 2-oxoheptylidene-tri-n-butylphosphorane were added to the solution, and the mixture was stirred at room temperature for 4.5 hours. After completion of the reaction, the solvent was distilled off from the reaction mixture, leaving a residue which was purified by silica gel column chromatography to yield 1.67 g of the desired compound as an oil.
IR spectrum (liquid film): $\nu_{max}=$ 1730, 1660, 1620 cm$^{-1}$.

NMR spectrum (CDCl$_3$): δ = −0.5 to −0.2 and 0.4 to 0.8 (three-membered ring),
2.1 (3H, singlet, —OCOC$\underline{H}_3$),
3.7 (3H, singlet, —COOC$\underline{H}_3$).

5.5 (1H, quartet, 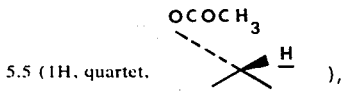 ), 6.1 (1H, doublet, 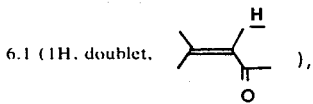 ), 6.8 (1H, quartet, 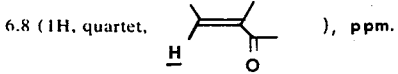 ), ppm.

Mass spectrum: 418 (M$^+$).

Preparation 8

Methyl 9α-acetoxy-15α-hydroxy-5(6),10(11)α-bis-methylene-prost-13-trans-enoate and methyl 9α-acetoxy-15β-hydroxy-5(6),10(11)α-bis-methylene-prost-13-trans-enoate

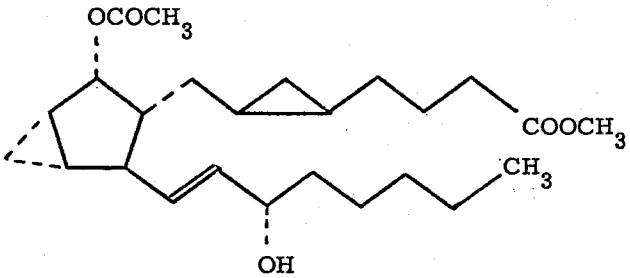

and

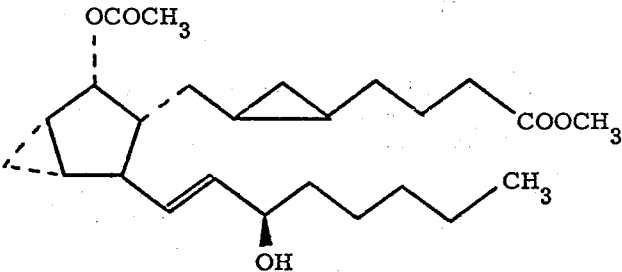

810 mg of methyl 9α-acetoxy-15oxo-5(6),10(11)α-bis-methyleneprost-13-trans-enoate was dissolved in 20 ml of anhydrous ether, 10 ml of anhydrous ether containing 140 mg of zinc borohydride were added to the solution, and the mixture was stirred at room temperature for 1.5 hours. After completion of the reaction, 20 ml of a saturated aqueous potassium sodium tartarate solution were added, and the organic and aqueous layers of the reaction mixture were separated. The organic layer was reserved and the aqueous layer was extracted with three 10 ml portions of ethyl acetate. The extracts and the reserved organic layer were combined and dried over anhydrous sodium sulphate. The solvent was distilled off, leaving 0.71 g of an oil which was purified by preparative thin-layer chromatography, developed with a mixture of n-hexane and ethyl acetate (2:1), giving 252 mg of methyl 9α-acetoxy-15α-hydroxy-5(6),10(11)α-bis-methyleneprost-13-trans-enoate, having the greater polarity, and 297 mg of methyl 9α-acetoxy-15β-hydroxy-5(6),10(11)α-bis-methyleneprost-13-trans-enoate, having the smaller polarity.

IR spectrum (liquid film): $\nu_{max} = 3440, 1735$ cm$^{-1}$.

NMR spectrum (CDCl$_3$): δ = −0.5 to −0.2 and 0.4 to 0.8 (three-membered ring),
2.1 (3H, singlet, —OCOC$\underline{H}_3$),
3.7 (3H, singlet, —COOC$\underline{H}_3$), 3.9–4.3 (1H, multiplet,  ), 5.2–5.6 (3H, multiplet,  ), ppm.

Mass spectrum: 420 (M$^+$), 360 (M$^+$ -60), 342 (M$^+$ -78).

Preparation 9

Methyl 9α-acetoxy-15α-(2-tetrahydropyranyl)oxy-5(6),10(11)α-bis-methyleneprost-13-trans-enoate

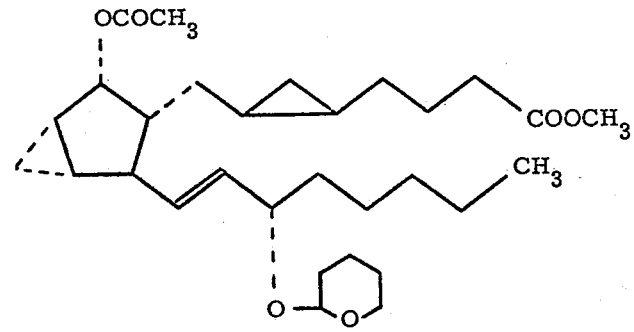

252 mg of methyl 9α-acetoxy-15α-hydroxy-5(6),10(11)α-bis-methyleneprost-13-trans-enoate were dissolved in 10 ml of anhydrous dichloromethane, 0.5 ml of dihydropyran and 1 ml of tetrahydrofuran containing 3 mg of p-toluenesulphonic acid were added under ice-cooling, and the mixture was stirred at room temperature for 30 minutes. The reaction was completed by addition of several drops of pyridine. The reaction mixture was washed with two 10 ml portions of water, and the organic layer was reserved. The washings were extracted with ether, and the ether extract was combined with the reserved organic layer and dried over anhydrous sodium sulphate. The solvent was distilled off, leaving 316 mg of the crude desired compound as an oil. IR spectrum (liquid film): $\nu_{max} = 1740, 1670$ cm$^{-1}$.

NMR spectrum (CDCl$_3$): δ = −0.5 to −0.2 and 0.5 to 0.8 (three-membered ring),
2.0 (3H, singlet, —OCOC$\underline{H}_3$),
3.6 (3H, singlet, —COOC$\underline{H}_3$), 3.2–4.3 (3H, multiplet, 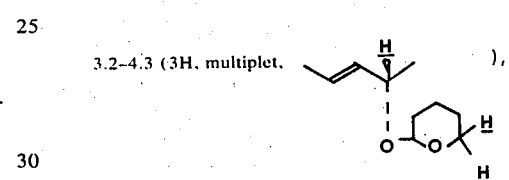 ), 4.7 (1H, multiplet, 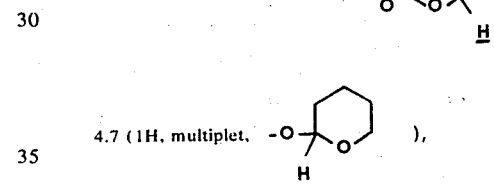 ), 5.2–5.6 (3H, multiplet, 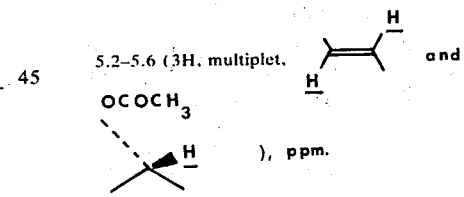 ), ppm.

Preparation 10

Methyl 9α-hydroxy-15α-(2-tetrahydropyranyl)oxy-5(6),10(11)α-bis-methyleneprost-13-trans-enoate

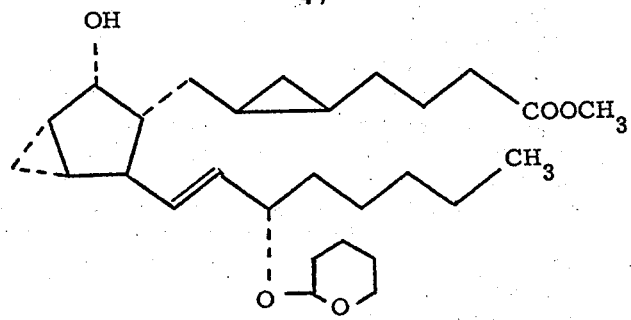

316 mg of methyl 9α-acetoxy-15α-(2-tetrahydropyranyl)oxy-5(6),10(11)α-bis-methyleneprost-13-trans-enoate were dissolved in 15 ml of methanol, 200 mg of anhydrous potassium carbonate were added to the solution, and the mixture was stirred at room temperature for 10 hours. After completion of the reaction, the solvent was distilled off from the reaction mixture under reduced pressure. The residue was acidified with 15 ml of aqueous acetic acid and extracted with ether. The extract was dried over anhydrous sodium sulphate, and diazomethane was added under ice-cooling until the yellow colour no longer disappeared. The solvent was distilled off, leaving a residue which was purified by silica gel column chromatography to yield 245 mg of the desired compound as an oil. IR spectrum (liquid film): $\nu_{max}$ = 3440, 1740 cm$^{-1}$.

NMR spectrum (CDCl$_3$): δ = −0.5 to −0.2 and 0.4 to 0.8 (three-membered ring),
3.6 (3H, singlet, —COOC$\underline{H}_3$),
3.2–4.3 (3H, multiplet, 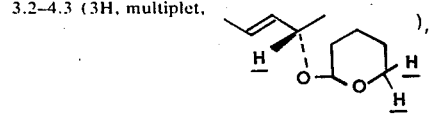 ),
4.5–4.8 (2H, multiplet, 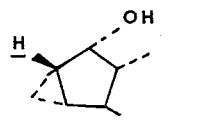 and 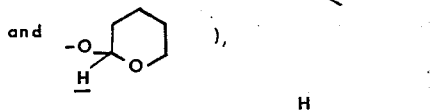 ),
4.9–5.8 (2H, multiplet, 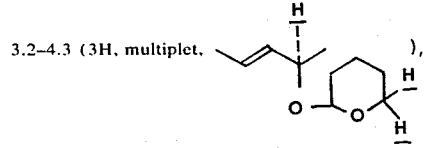 ), ppm.

Mass spectrum: 462(M$^+$).

Preparation 11

Methyl 9α-acetoxy-15β-(2-tetrahydropyranyl)oxy-5(6),10(11)α-bis-methyleneprost-13-trans-enoate

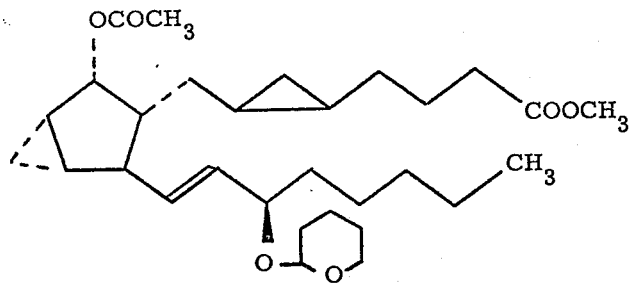

485 mg of methyl 9α-acetoxy-15β-hydroxy-5(6),10(11)α-bis-methyleneprost-13-trans-enoate were dissolved in 20 ml of anhydrous dichloromethane, 1.0 ml of dihydropyran and a catalytic amount of p-toluenesulphonic acid were added under ice-cooling, and the mixture was stirred for 5 minutes at the same temperature and then at room temperature for another 15 minutes. The reaction was completed by addition of several drops of pyridine to the reaction mixture. The reaction mixture was then treated in the same manner as in Preparation 9, to give 570 mg of the crude desired compounds as an oil. IR spectrum (liquid film): $\nu_{max}$ = 1740, 1670 cm$^{-1}$.

NMR spectrum (CDCl$_3$): δ = −0.5 to −0.2 and 0.5 to 0.8 (three-membered ring),
2.0 (3H, singlet, —OCOC$\underline{H}_3$),
3.6 (3H, singlet, —COOC$\underline{H}_3$), 3.2–4.3 (3H, multiplet, 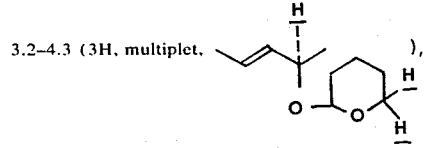 ), 4.7 (1H, multiplet, 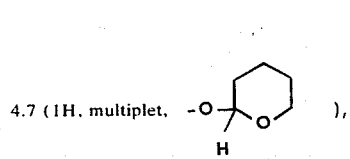 ), 5.2–5.6 (3H, multiplet, 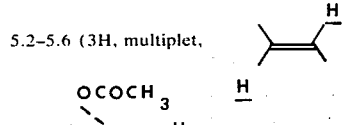 ), ppm.

Preparation 12

Methyl 9α-hydroxy-15β-(2-tetrahydropyranyl)oxy-5(6),10(11)α-bis-methyleneprost-13-trans-enoate

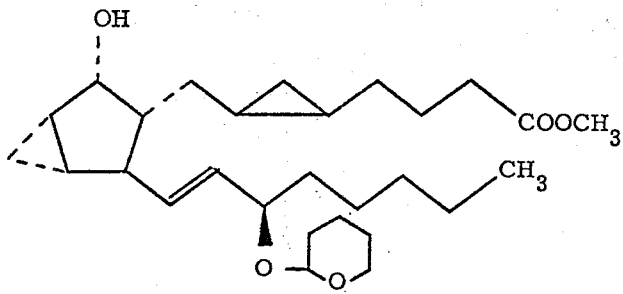

570 mg of methyl 9α-acetoxy-15β-(2-tetrahydropyranyl)oxy-5(6),10(11)α-bis-methyleneprost-13-trans-enoate were dissolved in 25 ml of methanol, 380 mg of anhydrous potassium carbonate were added to the solution, and the mixture was stirred at room temperature for 12 hours. After completion of the reaction, the reaction mixture was treated in the same manner as in Preparation 10, to give 427 mg of the desired compound as an oil.

The IR spectrum, NMR spectrum and Mass spectrum of this product were identical with those of the methyl 9α-hydroxy-15α-(2-tetrahydropyranyl)oxy-5(6),10(11)α-bis-methyleneprost-13-trans-enoate obtained in Preparation 10.

Preparation 13

9α-Hydroxy-15α-(2-tetrahydropyranyl)oxy-5(6),10(11)α-bis-methyleneprost-13-trans-enoic acid

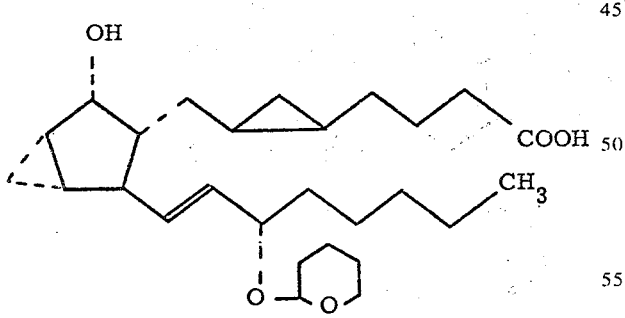

610 mg of methyl 9α-acetoxy-15α-(2-tetrahydropyranyl)oxy-5(6),10(11)α-bis-methyleneprost-13-trans-enoate were dissolved in 40 ml of methanol, 20 ml of 1N aqueous sodium hydroxide solution were added, and the mixture was stirred at room temperature for 7 hours. After completion of the reaction, the reaction mixture was acidified with saturated aqueous oxalic acid solution and extracted with five 20 ml portions of ether. The combined extracts were dried over anhydrous sodium sulphate, and the solvent was distilled off, leaving 594 mg of the crude desired compound as a pale yellow oil. IR spectrum (liquid film): $\nu_{max} = 3400, 1705$ cm$^{-1}$.

NMR spectrum (CDCl$_3$): δ = −0.5 to −0.2 and 0.5 to 0.8 (three membered ring), 3.2–4.2 (3H, multiplet, 4.6–4.8 (2H, multiplet, and

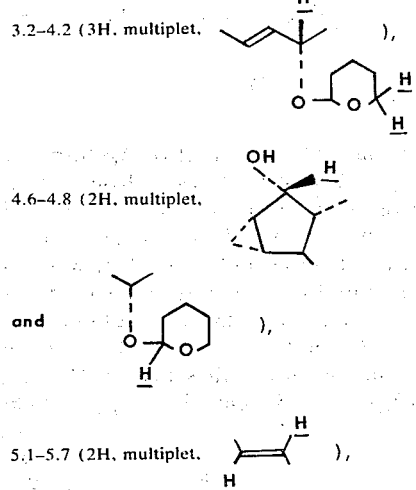

), 5.1–5.7 (2H, multiplet, ), 6.1–6.3 (2H, broad, singlet, —OH and —COOH), ppm.

Preparation 14

9α-Hydroxy-15β-(2-tetrahydropyranyl)oxy-5(6),10(11)α-bis-methyleneprost-13-trans-enoic acid

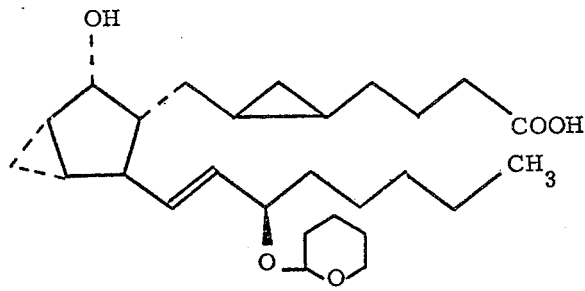

742 mg of methyl 9α-acetoxy-15β-(2-tetrahydropyranyl)oxy-5(6),10(11)α-bis-methyleneprost-13-trans-enoate were dissolved in 50 ml of methanol, 25 ml of 1N aqueous sodium hydroxide solution were added, and the mixture was stirred at room temperature for 8 hours. After completion of the reaction, the reaction mixture was treated in the same manner as in Preparation 13, to give 712 mg of the crude desired compound as an oil.

The IR spectrum and NMR spectrum of this product were identical with those of the 9α-hydroxy-15α-(2-tetrahydropyranyl)oxy-5(6),10(11)α-bis-methyleneprost-13-trans-enoic acid obtained in Preparation 13.

Prepartion 15

Methyl 9α-acetoxy-15-oxo-20-ethyl-5(6),10(11)α-bis-methyleneprost-13-trans-enoate

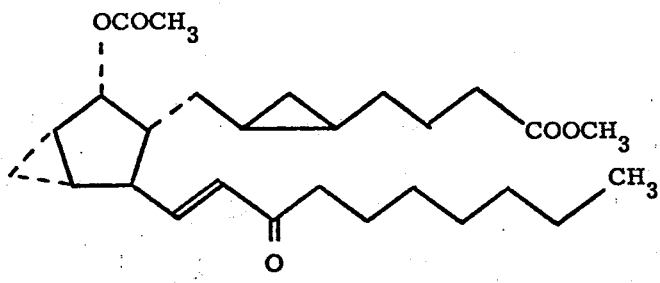

2.40 g of methyl 7-[2α-acetoxy-5β-formyl-3(4)α-methylenecyclopent-1α-yl]-5(6)-methyleneheptanoate were dissolved in 60 ml of anhydrous ether, 3.3 g of 2-oxononylidene-tri-n-butylphosphorane were added under a stream of argon, and the mixture was stirred at room temperature for 3 hours. After completion of the reaction, the reaction mixture was treated in the same manner as in Preparation 7, to give 3.04 g of the desired compound as an oil. IR spectrum (liquid film): $\nu_{max} = 1740, 1670, 1625$ cm$^{-1}$.

NMR spectrum (CDCl$_3$): $\delta = -0.5$ to $-0.2$ and $0.5$ to $0.8$ (three-membered ring), 2.1 (3H, singlet, —OCOC$\underline{H}_3$), 3.7 (3H, singlet, —COOC$\underline{H}_3$), 5.5 (1H, quartet, 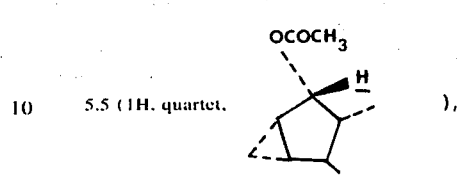 ), 6.1 (1H, doublet, 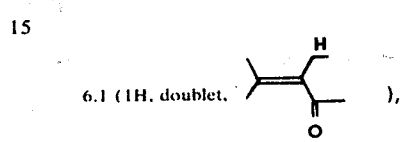 ), 6.8 (1H, quartet, 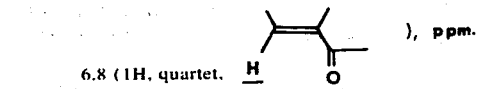 ), ppm.

Preparation 16

Methyl 9α-acetoxy-15α-hydroxy-20-ethyl-5(6),10(11)α-bis-methyleneprost-13-trans-enoate and methyl 9α-acetoxy-15β-hydroxy-20-ethyl-5(6),10(11)α-bis-methyleneprost-13-trans-enoate

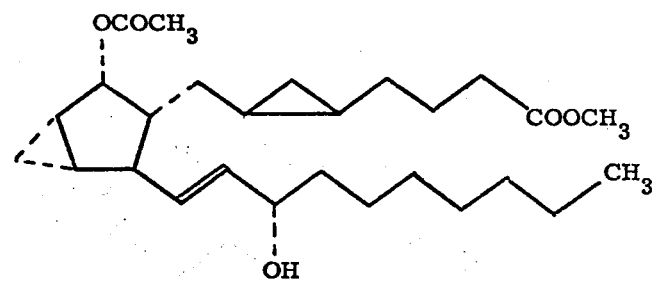

and

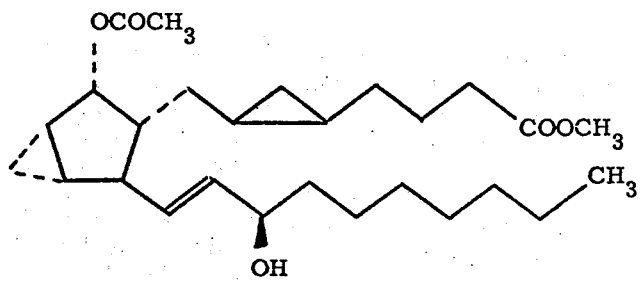

3.00 g of methyl 9α-acetoxy-15-oxo-20-ethyl-5(6),10(11)α-bis-methyleneprost-13-trans-enoate were dissolved in 20 ml of anhydrous ether, 80 ml of an ether solution containing 1 g of zinc borohydride were added under ice-cooling, and the mixture was stirred at room temperature for one hour. After completion of the reaction, the reaction mixture was treated in the same manner as in Preparation 8, to give 1.15 g of methyl 9α-acetoxy-15α-hydroxy-20-ethyl-5(6),10(11)α-bis-methyleneprost-13-trans-enoate, having the greater polarity, and 1.346 g of methyl 9α-acetoxy-15β-hydroxy-20-ethyl-5(6),10(11)α-bis-methyleneprost-13-trans-enoate, having the smaller polarity. IR spectrum (liquid film): $\nu_{max}$ = 3460, 1735 cm$^{-1}$.

NMR spectrum (CDCl$_3$): δ = −0.5 to −0.2 and 0.5 to 0.8 (three-membered ring), 2.1 (3H, singlet, —OCOC$\underline{H}_3$), 3.7 (3H, singlet, —COOC$\underline{H}_3$), 3.9–4.3 (1H, multiplet, 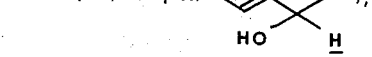 ), 5.2–5.7 (3H, multiplet, 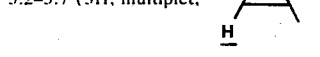

and 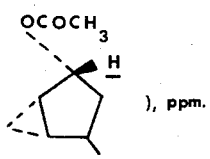 ), ppm.

Preparation 17

Methyl 9α-acetoxy-15α-(2-tetrahydropyranyl)oxy-20-ethyl-5(6),10(11)α-bis-methyleneprost-13-trans-enoate

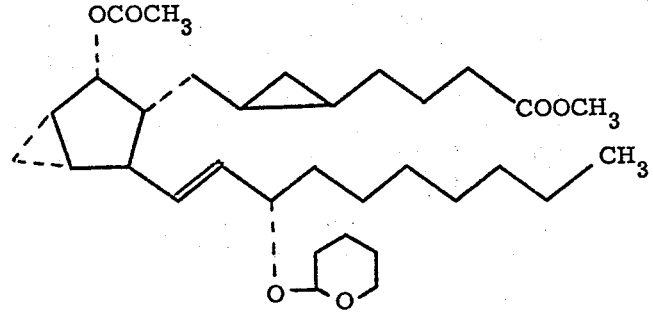

1.15 g of methyl 9α-acetoxy-15α-hydroxy-20-ethyl-5(6),10(11)α-bis-methyleneprost-13-trans-enoate were dissolved in 40 ml of anhydrous dichloromethane, 4.0 ml of dihydropyran and a catalytic amount of p-toluenesulphonic acid were added to the solution under ice-cooling, and the mixture was stirred for 15 minutes at the same temperature and then at room temperature for another 15 minutes. The reaction was completed by addition of 0.2 ml of pyridine, and the reaction mixture was then washed with two 30 ml portions of water. The organic layer was reserved, and the washings were extracted with 15 ml of ether. The extract was combined with the reserved organic layer and dried over anhydrous sodium sulphate. The solvent was distilled off, leaving 1.627 g of an oil, which was purified by column chromatography employing alumina (neutral Grade III) to yield 0.967 g of the desired compound as an oil. IR spectrum (liquid film): $\nu_{max}$ = 1735 cm$^{-1}$.

NMR spectrum (CDCl$_3$): δ = −0.5 to −0.2 and 0.5 to 0.8 (three-membered ring), 2.0 (3H, singlet, —OCOC$\underline{H}_3$), 3.6 (3H, singlet, —COOC$\underline{H}_3$), 3.2–4.3 (3H, multiplet, 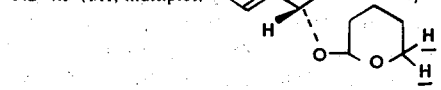 ), 4.7 (1H, multiplet,  ), 5.2–5.7 (3H, multiplet, 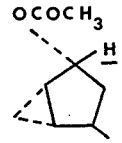

and 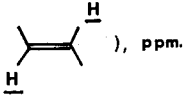 ), ppm.

Preparation 18

9α-Hydroxy-15α-(2-tetrahydropyranyl)oxy-20-ethyl-5(6),10(11)α-bis-methyleneprost-13-trans-enoic acid

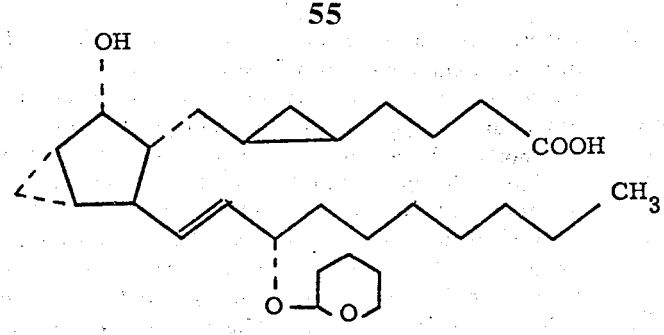

960 mg of methyl 9α-acetoxy-15α-(2-tetrahydropyranyl)oxy-20-ethyl-5(6),10(11)α-bis-methyleneprost-13-trans-enoate were dissolved in 50 ml of methanol, 15 ml of 1N aqueous sodium hydroxide solution were added, and the mixture was stirred at room temperature for 8 hours. After completion of the reaction, the reaction mixture was acidified with saturated aqueous oxalic acid and extracted with five 40 ml portions of ether. The combined extracts were dried over anhydrous sodium sulphate, and the solvent was distilled off, to give crystals. The crystals thus obtained were recrystallized from ethyl acetate-n-hexane to yield 929 mg of the desired compound as white crystals, m.p. 70°–71°C. IR spectrum (liquid film): $\nu_{max} = 3400, 1705$ cm$^{-1}$.

NMR spectrum (CDCl$_3$): δ = −0.5 to −0.2 and 0.5 to 0.8 (three-membered ring), 3.2–4.3 (3H, multiplet, 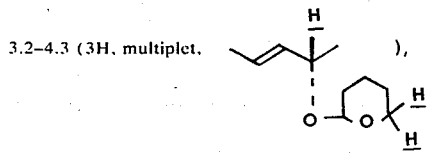 ), 4.6–4.8 (2H, multiplet, 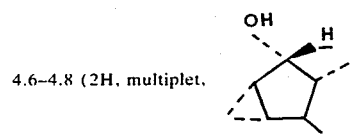 )

and 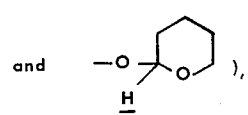 ),

| -continued |
|---|
| 5.2–5.8 (4H, multiplet, 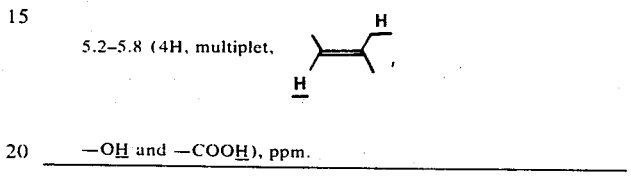 , |
| —O$\underline{H}$ and —COO$\underline{H}$), ppm. |

Preparation 19

Methyl 9α-acetoxy-15β-(2-tetrahydropyranyl)oxy-20-ethyl-5(6),10(11)α-bis-methyleneprost-13-trans-enoate

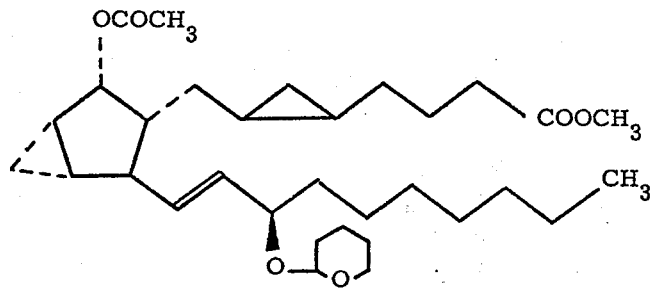

1.346 g of methyl 9α-acetoxy-15β-hydroxy-20-ethyl-5(6),10(11)α-bis-methyleneprost-13-trans-enoate were dissolved in 40 ml of anhydrous dichloromethane, 40 ml of dihydropyran and a catalytic amount of p-toluenesulphonic acid were added under ice-cooling, and the mixture was stirred at the same temperature for 15 minutes and then at room temperature for another 15 minutes. The reaction was completed by adding several drops of pyridine, and the reaction mixture was treated in the same manner as in Preparation 17, to give 1.272 g of the desired compound as an oil.

The IR spectrum and NMR spectrum of the product were identical with those of the methyl 9α-acetoxy-15α-(2-tetrahydropyranyl)-oxy-20-ethyl-5(6),10(11)α-bis-methyleneprost-13-trans-enoate obtained in Preparation 17.

Preparation 20

9α-Hydroxy-15β-(2-tetrahydropyranyl)oxy-20-ethyl-5(6),10(11)α-bis-methyleneprost-13-trans-enoic acid

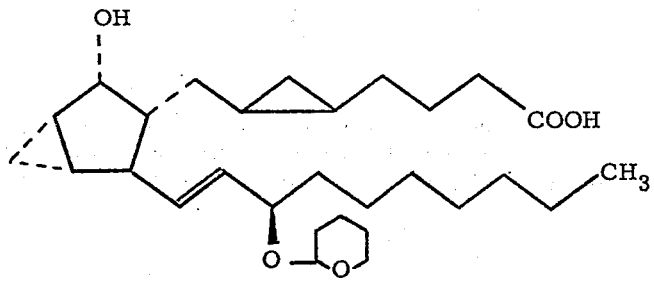

1.263 g of methyl 9α-acetoxy-15β-(2-tetrahydropyranyl)oxy-20-ethyl-5(6),10(11)α-bis-methyleneprost-13-trans-enoate were dissolved in 50 ml of methanol, 15 ml of 1N aqueous sodium hydroxide solution were added, and the mixture was stirred at room temperature for 8 hours. After completion of the reaction, the reaction mixture was treated in the same manner as in Preparation 18, to give 0.703 g of the desired compound as white crystals, m.p. 54°–55°C.

The IR spectrum and NMR spectrum of the product were identical with those of the 9α-hydroxy-15α-(2-tetrahydropyranyl)oxy-20-ethyl-5(6),10(11)α-bis-methyleneprost-13-trans-enoic acid obtained in Preparation 18.

Preparation 21

Methyl 9α-acetoxy-15-oxo-20-n-butyl-5(6),10(11)α-bis-methyleneprost-13-trans-enoate

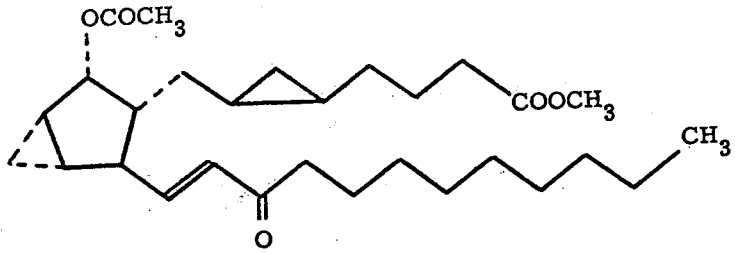

2.37 g of methyl 7-[2α-acetoxy-5β-formyl-3(4)α-methylenecyclopent-1α-yl]-5(6)-methyleneheptanoate were dissolved in 60 ml of anhydrous ether, 3.70 g of 2-oxoundecylidene-tri-n-butylphosphorane were added under a stream of argon, and the mixture was stirred at room temperature for 3 hours. After completion of the reaction, the reaction mixture was treated in the same manner as in Preparation 7, to give 3.23 g of the desired compound as an oil. IR spectrum (liquid film): $\nu_{max} = 1735, 1670, 1620$ cm$^{-1}$.

NMR spectrum (CDCl$_3$): δ = −0.5 to −0.2 and 0.5 to 0.8 (three-membered ring), 2.1 (3H, singlet, —OCOC$\underline{H}_3$), 3.7 (3H, singlet, —COOC$\underline{H}_3$), 5.5 (1H, quartet, 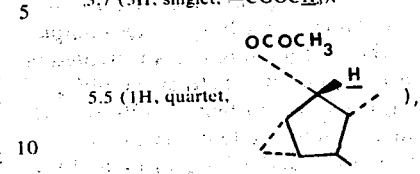 ), 6.1 (1H, doublet, 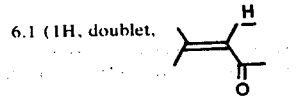 ), 6.8 (1H, quartet, 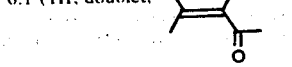 ), ppm.

Preparation 22

Methyl 9α-acetoxy-15α-hydroxy-20-n-butyl-5(6),10(11)α-bis-methyleneprost-13-trans-enoate and methyl 9α-acetoxy-15β-hydroxy-20-n-butyl-5(6),10(11)α-bis-methyleneprost-13-trans-enote

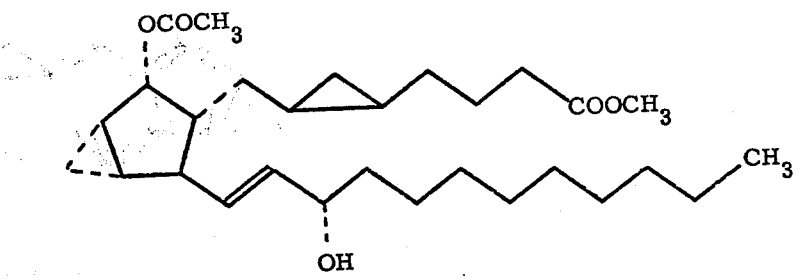

and

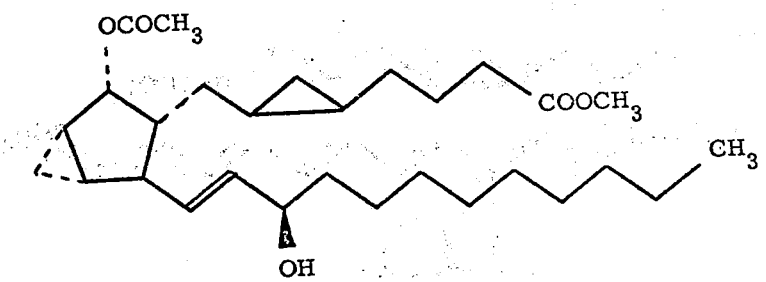

3.18 g of methyl 9α-acetoxy-15-oxo-20-n-butyl-5(6),10(11)α-bis-methyleneprost-13-trans-enoate were dissolved in 20 ml of anhydrous ether, 80 ml of anhydrous ether containing 1 g of zinc borohydride were added under ice-cooling, and the mixture was stirred at room temperature for 1 hour. After completion of the reaction, the reaction mixture was treated in the same manner as in Preparation 8, to give 0.995 g of methyl 9α-acetoxy-15α-hydroxy-20-n-butyl-5(6),10(11)α-bis-methyleneprost-13-trans-enoate, having the greater polarity, and 1.23 g of methyl 9α-acetoxy-15β-hydroxy-20-n-butyl-5(6),10(11)α-bis-methyleneprost-13-trans-enoate, having the smaller polarity. IR spectrum (liquid film): $\nu_{max}$ = 3440, 1735 cm$^{-1}$.

NMR spectrum (CDCl$_3$): δ = −0.5 to −0.2 and 0.5 to 0.8 ((three-membered ring),
2.1 (3H, singlet, —OCOC$\underline{H}_3$),
3.7 (3H, singlet, —COOC$\underline{H}_3$), 3.9–4.3 (1H, multiplet,  ), 5.2–5.7 (3H, multiplet, 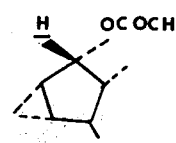

and 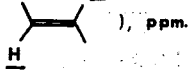 ), ppm.

0.986 g of methyl 9α-acetoxy-15α-hydroxy-20-n-butyl-5(6),10(11)α-bis-methyleneprost-13-trans-enoate were dissolved in 40 ml of anhydrous dichloromethane, 3.0 ml of dihydropyran and a catalytic amount of p-toluenesulphonic acid were added under ice-cooling, and the mixture was stirred at the same temperature for 5 minutes and then at room temperature for 30 minutes. The reaction was completed by adding several drops of pyridine, and the reaction mixture was treated in the same manner as in Preparation 17, to give 1.110 g of the desired compound as an oil. IR spectrum (liquid film): $\nu_{max}$ = 1735 cm$^{-1}$.

NMR spectrum (CDCl$_3$): δ = −0.5 to −0.2 and 0.5 to 0.8 ((three-membered ring),
2.0 (3H, singlet, —OCOC$\underline{H}_3$),
3.6 (3H, singlet, —COOC$\underline{H}_3$), 3.2–4.3 (3H, multiplet, 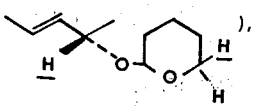 ), 4.7 (1H, multiplet, 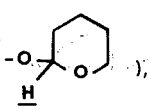 ), 5.2–5.7 (3H, multiplet, 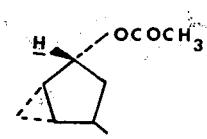

and 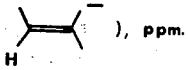 ), ppm.

Preparation 24

9α-Hydroxy-15α-(2-tetrahydropyranyl)oxy-20-n-butyl-5(6),10(11)α-bis-methyleneprost-13-trans-enoic acid

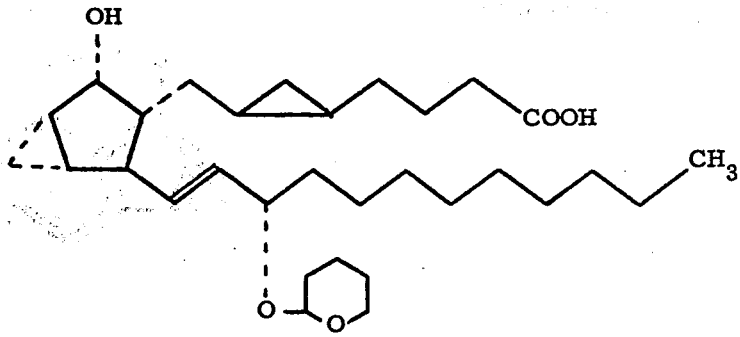

Methyl 9α-acetoxy-15α-(2-tetrahydropyranyl)oxy-20-n-butyl-5(6),10(11)α-bis-methyleneprost-13-trans-enoate

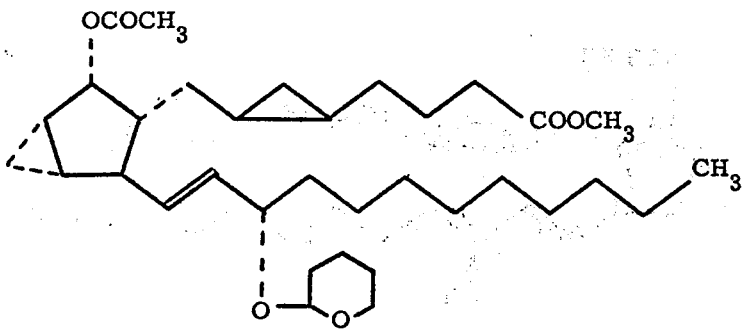

1.09 g of methyl 9α-acetoxy-15α-(2-tetrahydropyranyl)oxy-20-n-butyl-5(6),10(11)α-bis-methyleneprost-13-trans-enoate were dissolved in 80 ml of methanol, 40 ml of 1N aqueous sodium hydroxide solution were added, and the mixture was stirred at room temperature for 7 hours. After completion of the reation, the reaction mixture was treated in the same manner as in Preparation 18, to give 1.023 g of the crude desired compound as an oil. IR spectrum (liquid film): $\nu_{max}$ = 3440, 1705 cm$^{-1}$.

NMR spectrum (CDCl$_3$): δ = −0.5 to −0.2 and 0.5 to 0.8 (three-membered ring), 3.2–4.2 (3H, multiplet, 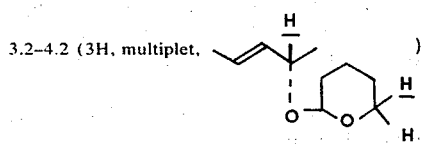 ), 1.230 g of methyl 9α-acetoxy-15β-hydroxy-20-n-butyl-5(6),10(11)α-bis-methyleneprost-13-trans-enoate were dissolved in 40 ml of anhydrous dichloromethane, 4.0 ml of dihydropyran and a catalytic amount of p-toluenesulphonic acid were added under ice-cooling, and the mixture was stirred at the same temperature for 5 minutes and then at room temperature for 30 minutes. After completion of the reaction, the reaction mixture was treated in the same manner as in Preparation 17, to give 1.272 g of the desired compound as an oil.

The IR spectrum and NMR spectrum of the product were identical with those of the methyl 9α-acetoxy-15α-(2-tetrahydropyranyl)-oxy-20-n-butyl-5(6),10(11)α-bis methyleneprost-13-trans-enoate obtained in Preparation 23.

Preparation 26.

9α-Hydroxy-15β-(2-tetrahydropyranyl)oxy-20-n-butyl-5(6),10(11)α-bis-methyleneprost-13-trans-enoic acid

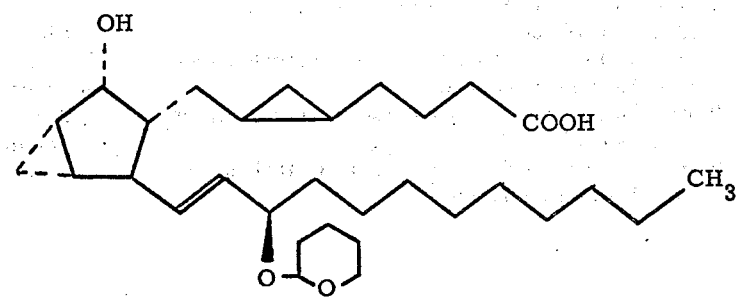

4.6–4.8 (2H, multiplet, and 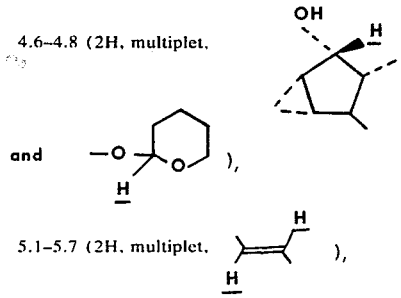 ), 5.1–5.7 (2H, multiplet, ), 6.5 (2H, borad singlet, —O$\underline{H}$ and —COO$\underline{H}$), ppm.

Preparation 25

Methyl 9α-acetoxy-15β-(2-tetrahydropyranyl)oxy-20-n-butyl-5(6),10(11)α-bis-methyleneprost-13-trans-enoate 1.218 g of methyl 9α-acetoxy-15β-(2-tetrahydropyranyl)oxy-20-n-butyl-5(6),10(11)α-bis-methyleneprost-13-trans-enoate were dissolved in 50 ml of methanol, 15 ml of 1N aqueous sodium hydroxide solution were added, and the mixture was stirred at room temperature for 8 hours. After completion of the reaction, the reaction mixture was treated in the same manner as in Preparation 18, to give 1.012 g of the crude desired compound as an oil.

The IR spectrum and NMR spectrum of the product were identical with those of the 9α-hydroxy-15α-(2-tetrahydropyranyl)oxy-20-n-butyl-5(6),10(11)α-bis-methyleneprost-13-trans-enoic acid obtained in Preparation 24.

We claim:

1. A compound selected from prostenoic acid derivatives having the formula

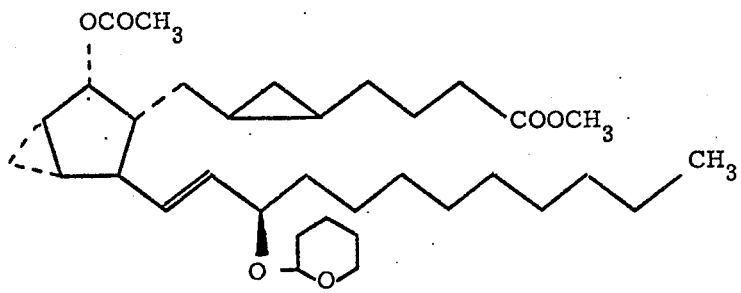

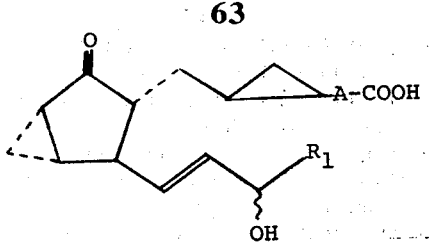

wherein
A is a linking group selected from the class consisting of a direct single bond and an alkylene group having from 1 to 8 carbon atoms; and
$R^1$ is an alkyl group having from 1 to 10 carbon atoms;
and pharamaceutically acceptable salts thereof.

2. A compound according to claim 1, wherein $R^1$ is an alkyl group having from 4 to 10 carbon atoms.

3. A compound according to claim 1, wherein A is an alkylene group having from 1 to 5 carbon atoms.

4. A prostenoic acid derivative selected from the group consisting of:

9-oxo-15α-hydroxy-5(6),10(11)α-bis-methyleneprost-13-trans-enoic acid,
9-oxo-15α-hydroxy-5(6),10(11)α-bis-methyleneisoprost-13-trans-enoic acid,
9-oxo-15β-hydroxy-5(6),10(11)α-bis-methyleneprost-13-trans-enoic acid,
9-oxo-15β-hydroxy-5(6),10(11)α-bis-methyleneisoprost-13-trans-enoic acid,
9-oxo-15α-hydroxy-20-ethyl-5(6),10(11)α-bis-methyleneprost-13-trans-enoic acid,
9-oxo-15β-hydroxy-20-ethyl-5(6),10(11)α-bis-methyleneprost-13-trans-enoic acid,
9-oxo-15α-hydroxy-20-n-butyl-5(6),10(11)α-bis-methyleneprost-13-trans-enoic acid, and
9-oxo-15β-hydroxy-20-n-butyl-5(6),10(11)α-bis-methyleneprost-13-trans-enoic acid.

5. 9-Oxo-15α-hydroxy-5(6),10(11)α-bis-methyleneprost-13-trans-enoic acid of the formula of claim 1.

6. 9-Oxo-15α-hydroxy-5(6),10(11)α-bis-methyleneisoprost-13-trans-enoic acid of the formula of claim 1.

7. 9-Oxo-15β-hydroxy-5(6),10(11)α-bis-methyleneprost-13-trans-enoic acid of the formula of claim 1.

8. 9-Oxo-15β-hydroxy-5(6),10(11)α-bis-methyleneisoprost-13-trans-enoic acid of the formula of claim 1.

9. 9-Oxo-15α-hydroxy-20-ethyl-5(6),10(11)α-bis-methyleneprost-13-trans-enoic acid of the formula of claim 1.

10. 9-Oxo-15β-hydroxy-20-ethyl-5(6),10(11)α-bis-methyleneprost-13-trans-enoic acid of the formula of claim 1.

11. 9-Oxo-15α-hydroxy-20-n-butyl-5(6),10(11)α-bis-methyleneprost-13-trans-enoic acid of the formula of claim 1.

12. 9-Oxo-15β-hydroxy-20-n-butyl-5(6),10(11)α-bis-methyleneprost-13-trans-enoic acid of the formula of claim 1.

* * * * *

UNITED STATES PATENT OFFICE
CERTIFICATE OF CORRECTION

PATENT NO. : 3,971,825
DATED : July 27, 1976
INVENTOR(S) : KIYOSHI SAKAI et al

It is certified that error appears in the above-identified patent and that said Letters Patent are hereby corrected as shown below:

Column 25, line 1, at "(4)":

replace " 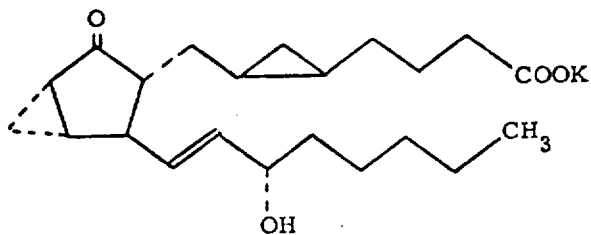 "

with --- 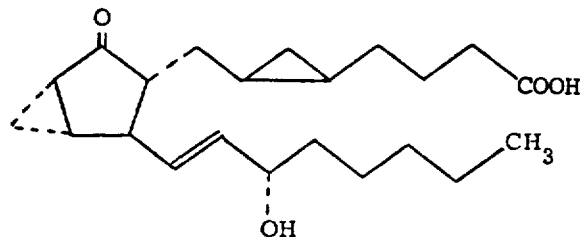 ---.

Signed and Sealed this

Eleventh Day of October 1977

[SEAL]

Attest:

RUTH C. MASON
Attesting Officer

LUTRELLE F. PARKER
Acting Commissioner of Patents and Trademarks